US010982934B2

(12) United States Patent
Ostovich

(10) Patent No.: US 10,982,934 B2
(45) Date of Patent: Apr. 20, 2021

(54) FIREARMS MARKSMANSHIP IMPROVEMENT PRODUCT AND RELATED SYSTEM AND METHODS

(71) Applicant: Robert Dewey Ostovich, Palm Bay, FL (US)

(72) Inventor: Robert Dewey Ostovich, Palm Bay, FL (US)

(*) Notice: Subject to any disclaimer, the term of this patent is extended or adjusted under 35 U.S.C. 154(b) by 499 days.

(21) Appl. No.: 15/882,047

(22) Filed: Jan. 29, 2018

(65) Prior Publication Data

US 2018/0216916 A1 Aug. 2, 2018

Related U.S. Application Data

(60) Provisional application No. 62/451,474, filed on Jan. 27, 2017.

(51) Int. Cl.
*F41G 3/26* (2006.01)
*G09B 5/02* (2006.01)
(Continued)

(52) U.S. Cl.
CPC ............ *F41G 3/2605* (2013.01); *F41A 33/02* (2013.01); *F41A 33/06* (2013.01); *F41G 3/26* (2013.01);
(Continued)

(58) Field of Classification Search
CPC .......... F41A 33/00; F41A 33/02; F41A 33/06; F41G 3/26; G09B 19/00; F41J 5/00; A61B 5/0205; A61B 5/486; A61B 5/4561
See application file for complete search history.

(56) References Cited

U.S. PATENT DOCUMENTS 8,360,776 B2 1/2013 Manard
8,794,967 B2 8/2014 Sargent
(Continued)

FOREIGN PATENT DOCUMENTS

WO WO2015116675 A1 8/2015

OTHER PUBLICATIONS

Robert D. Ostovich, Mr. O Fire Arms Training Targets, Jan. 1, 2012, Palm Bay, Florida, USA.
(Continued)

*Primary Examiner* — Jerry-Daryl Fletcher
(74) *Attorney, Agent, or Firm* — George P. Zies; William A. Harding

(57) ABSTRACT

A firearms marksmanship training system comprising a shooter observation booth characterized by intended shooting technique data and comprising a plurality of cameras configured to receive observed shooting technique data; a diagnostic target characterized by intended projectile strike data and configured to receive observed projectile strike data; and a shooter data analysis tool configured to determine at least one performance indication, defined as a shooting flaw, using a variance of the intended shooting technique data from the observed shooting technique data and a displacement of the intended projectile strike data from the observed projectile strike data, to determine, using a plurality of known shooting flaws associated with a plurality of known corrective measures, a probability of correction of the shooting flaw for at least one of the known corrective measures, defined as an applied corrective measure, and to provide sensory guidance as to the applied corrective measure.

20 Claims, 11 Drawing Sheets

(51) Int. Cl.
  *F41A 33/02*    (2006.01)
  *F41A 33/06*    (2006.01)
  *A61B 5/103*    (2006.01)
  *A61B 5/0205*   (2006.01)
  *A61B 5/00*     (2006.01)

(52) U.S. Cl.
  CPC .............. *G09B 5/02* (2013.01); *A61B 5/0077* (2013.01); *A61B 5/02055* (2013.01); *A61B 5/1036* (2013.01); *A61B 5/4561* (2013.01); *F41G 3/2655* (2013.01)

(56) References Cited

U.S. PATENT DOCUMENTS

| | | | |
|---|---|---|---|
| 9,033,711 B2 | 5/2015 | Guenther | |
| 2008/0032268 A1* | 2/2008 | Farrell | F41A 17/06 434/16 |
| 2010/0240015 A1 | 9/2010 | Chung | |
| 2010/0241464 A1* | 9/2010 | Amigo | A61B 5/1038 705/4 |
| 2011/0105859 A1* | 5/2011 | Popovic | A61B 5/02405 600/301 |
| 2012/0171644 A1* | 7/2012 | Moser | G09B 9/003 434/16 |
| 2012/0258432 A1 | 10/2012 | Weissler | |
| 2014/0092245 A1 | 4/2014 | Moore | |
| 2014/0106311 A1 | 4/2014 | Skrepetos | |
| 2015/0123346 A1 | 5/2015 | Mason | |
| 2015/0285592 A1 | 10/2015 | Napier | |
| 2016/0298930 A1* | 10/2016 | Squire | F41G 3/26 |
| 2018/0031353 A1* | 2/2018 | Skrepetos | F41G 3/2611 |

OTHER PUBLICATIONS

Robert D. Ostovich, Mr. O's Training Target Booklet, 2015, Palm Bay, Florida, USA.

* cited by examiner

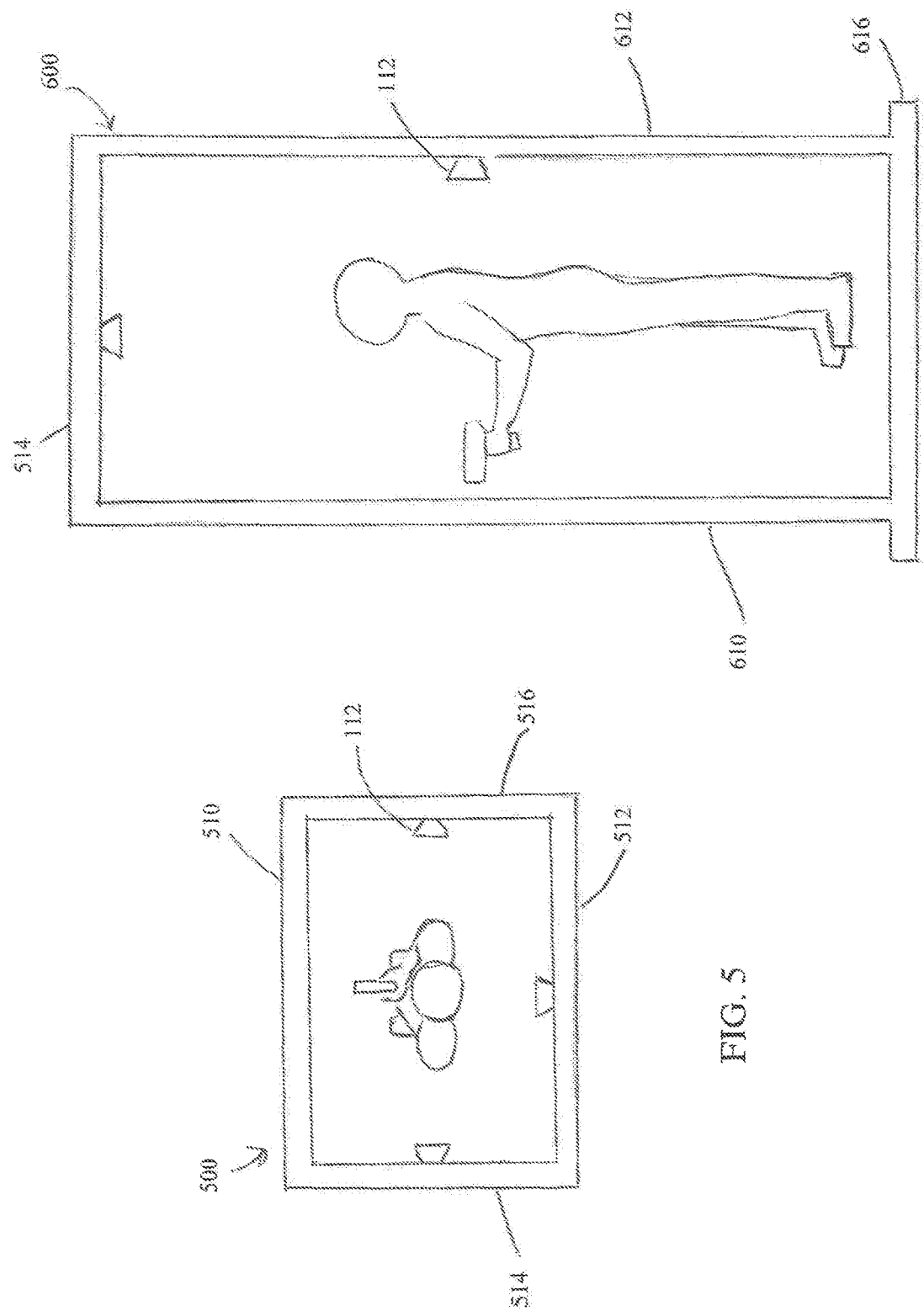

FIREARMS MARKSMANSHIP IMPROVEMENT PRODUCT AND RELATED SYSTEM AND METHODS

RELATED APPLICATIONS

The present application claims the benefit of U.S. Provisional Patent Application Ser. No. 62/451,474 titled FIREARMS MARKSMANSHIP IMPROVEMENT PRODUCT AND RELATED SYSTEM AND METHODS filed by the inventor of the present invention on Jan. 27, 2017, the entire contents of which are incorporated herein by reference.

FIELD OF THE INVENTION

The present invention relates to the field of firearms marksmanship and, more specifically, to systems and methods for correcting observed and deduced flaws in the handling, aiming and firing of a firearm.

BACKGROUND OF THE INVENTION

Ever since firearms were first invented sometime in the thirteenth century, the effectiveness of any firearm has been intrinsically intertwined with the ability to accurately and consistently impact a target with a projectile launched from the firearm. Because humans fire firearms, human-centric variables directly impact the accuracy and consistency with which a projectile launched from a firearm hits a target. While there are certainly mechanical components involved in the accuracy and consistency with which projectiles launched from firearms hit their targets, human factors are more commonly the sources of inaccuracy and inconsistency.

The human-induced inaccuracy and inconsistency with which projectiles launched from firearms hit their targets not only compromises the effectiveness of firearms, but also increases the costs associated with hunting, personal protection, law enforcement and military campaigns. Each projectile that is launched from a firearm has a cost associated with it. The more accurately and consistently a firearm is fired, the fewer projectiles need to be launched at a given target in order to hit that target. The fewer projectiles that are launched at a target in order to hit that target, the less expensive it is to use the firearm.

There are other costs associated with a firearm that is inaccurately and inconsistently fired. Projectiles that are inaccurately and inconsistently launched from a firearm may strike unintended targets. When those unintended targets are personal property, the costs associated with the inaccurately and inconsistently launched projectile are measured by the cost of repairing or replacing the personal property that was unintentionally hit. When those unintended targets are humans or other irreplaceable targets, however, the costs associated with the inaccurately and inconsistently launched projectile are immeasurable.

Other costs associated with projectiles inaccurately and inconsistently launched from firearms include the cost of retraining shooters. When a hunter, a law enforcement officer, a combatant, a gun-owner or other shooter is unable to accurately and consistently hit intended targets with projectiles the shooter launches from firearms, the shooter is often subjected to repeated training exercises in an effort to correct the shooter's inaccuracies and inconsistencies. Trainers charge a fee for their services, on top of the cost of the projectiles fired during training. In addition to the costs directly associated with retraining a shooter, indirect costs of retraining include the loss of man-hours while the shooter-in-training is unable to perform her normal occupation or profession.

In addition to the financial costs associated with inaccurately and inconsistently launched projectiles, there are also psychological costs. When a shooter is unable to accurately and consistently launch projectiles from a firearm at a target, that shooter, and others with whom the shooter interacts, may lose confidence in the shooter's abilities with a firearm. The loss of confidence in the shooter's abilities can negatively impact the effectiveness of a law enforcement unit, a military unit, or a family unit.

While various firearms training solutions are known in the art, none of them is reliably effective in observing, deducing and correcting the full range of flaws responsible for projectiles inaccurately and inconsistently launched from firearms. For example, not all firearms training courses analyze the stance of the shooter or the shooter's grip in a determination of the corrective action necessary to resolve inaccuracies and inconsistencies in shooting performance. Even those firearms training courses that do analyze shooter stance and shooter grip typically rely solely upon unaided observations of the human eye. Likewise, some known firearms training courses fail to deduce flaws in shooting technique determinable from the placement of projectile strikes on a target.

In cases where known firearms training courses are successful in observing or deducing flaws in shooting technique, these firearms training courses do not rigorously and repeatably determine the appropriate corrective action necessary to resolve the full range of flaws responsible for inaccuracies and inconsistencies in shooting performance. Whether such failure results from an inability to ascertain all of the factors impacting shooting performance or a lack of understanding of the methods of shooting technique correction, known firearms training courses fall short of being able to resolve the full range of flaws responsible for inaccuracies and inconsistencies in shooting performance.

Accordingly, a need exists for improved methods and systems for providing reliable and effective analysis of shooting technique, while at the same time providing accurate corrective action to resolve the full range of flaws responsible for inaccuracies and inconsistencies in shooting performance.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to systems and processes for transforming observed shooting-technique flaws and observed off-target projectile strikes into recommended marksmanship improvement corrective measures. Such transformation of inaccuracy data into corrective measures may advantageously expand the commercial usefulness of firearms to a consumer. The products of such systems and processes may advantageously be enjoyed by military personnel, law enforcement personnel and those who use firearms for competition, for hunting and for personal defense.

A firearms marksmanship training system may comprise a shooter observation booth, a diagnostic target and a shooter data analysis tool. The shooter observation booth may be characterized by intended shooting technique data and may comprise a plurality of cameras configured to receive a first subset of observed shooting technique data. The diagnostic target may be characterized by intended projectile strike data and may be configured to receive observed projectile strike data. The shooter data analysis tool may be configured to determine at least one performance indication, defined as a shooting flaw, to determine a probability of correction of the shooting flaw for at least one of the known corrective measures, and to provide sensory guidance as to the applied corrective measure. The at least one performance indication may be determined using a variance of the intended shooting technique data from the observed shooting technique data and a displacement of the intended projectile strike data from the observed projectile strike data. The probability of correction of the shooting flaw for at least one of the known corrective measures, defined as an applied corrective measure, may be determined using a plurality of known shooting flaws, defined as a plurality of identified shooting flaws, associated with a plurality of known corrective measures, defined as a plurality of identified corrective measures. The shooter data analysis tool may further comprise a user interface configured to display the sensory guidance. The first subset of observed shooting technique data may be selected from the group consisting of a stance, a head position, a hand position, a grip, and a trigger pull. The shooter observation booth may further comprise a diagnostic firearm surrogate having at least one of a grip pressure sensor configured to receive the grip and a trigger pressure sensor configured to receive the trigger pull. The shooter observation booth may further comprise a floor pressure sensor configured to receive a second subset of observed shooting technique data selected from the group consisting of a stance and a weight distribution. The shooter observation station may further comprise a vital signs sensor configured to receive a third subset of observed shooting technique data selected from the group consisting of a heartrate and a body temperature.

A firearms marksmanship training method may comprise the steps of receiving intended shooting technique data and a first subset of observed shooting technique data using a shooter observation booth comprising a plurality of cameras; receiving intended projectile strike data and observed projectile strike data using a diagnostic target; and determining, using a shooter data analysis tool, at least one performance indication, defined as a shooting flaw, as a variance of the intended shooting technique data from the observed shooting technique data and a displacement of the intended projectile strike data from the observed projectile strike data; determining, using the shooter data analysis tool, a probability of correction of the shooting flaw for an applied corrective measure selected from a plurality of known corrective measures, defined as a plurality of identified corrective measures, associated with a plurality of known shooting flaws, defined as a plurality of identified shooting flaws; and providing, using the shooter data analysis tool, sensory guidance as to the applied corrective measure. The shooter data analysis tool may comprise a central processing unit (CPU) and a non-transitory computer-readable storage medium accessible through the CPU. The non-transitory computer-readable storage medium may comprise a plurality of instructions executed by the CPU. The firearms marksmanship training method may further comprise the steps of selecting the first subset of observed shooting technique data from the group consisting of a stance, a head position, a hand position, a grip, and a trigger pull; receiving the grip and the trigger pressure from a diagnostic firearm surrogate wherein the shooter observation station comprises the diagnostic firearm surrogate having at least one of a grip pressure sensor configured to receive the grip and a trigger pressure sensor configured to receive the trigger pull; receiving a stance and a weight distribution from a floor pressure sensor wherein the shooter observation booth comprises the floor pressure sensor configured to receive a second subset of observed shooting technique data selected from the group consisting of the stance and the weight distribution; receiving a heartrate and a body temperature from a vital signs sensor wherein the shooter observation station comprises the vital signs sensor configured to receive a third subset of observed shooting technique data selected from the group consisting of the heartrate and the body temperature; selecting the observed projectile strike data from the group consisting of a low projectile strike, a high projectile strike, a left-of-center projectile strike, a right-of-center projectile strike, a low-and-left-of-center projectile strike, a low-and-right-of-center projectile strike, a high-and-left-of-center projectile strike, and a high-and-right-of-center projectile strike; selecting the plurality of known shooting flaws from the group consisting of a shooter anticipatorily reacting to a retort of a firearm, the shooter incorrectly locating a trigger-finger on a trigger of the firearm, the shooter gripping the firearm with too much an incorrect amount of force, the shooter gripping the firearm with an uneven force, the shooter tensing shoulders while shooting the firearm, the shooter incorrectly standing while shooting the firearm, the shooter compromising a straight line between an eye of the shooter and a rear sight of the firearm and a front sight of the firearm and a target, the shooter focusing on a point on the straight line other than the front sight, the shooter failing to maintain control of the trigger, the shooter failing to counteract a recoil of the firearm, the shooter an incorrect amount of slack in a wrist of the shooter, the shooter squeezing the trigger with an incorrect amount of force, and the shooter failing to center the front sight within the rear sight; selecting the plurality of known corrective actions from the group consisting of the shooter not anticipating the retort of the firearm, the shooter correctly locating the trigger-finger on the trigger of the firearm, the shooter gripping the firearm with a force of a handshake, the shooter gripping the firearm with an even force, the shooter relaxing shoulders while shooting the firearm, the shooter standing with feet apart shoulder-width with knees slightly bent sitting straight down slightly with head straight up, the shooter maintaining control of the trigger release, the shooter pulling the firearm down to counteract recoil, the shooter keeping wrist snug while shooting, the shooter squeezing the trigger straight back to a web of a hand of the shooter with an even force, the shooter maintaining a straight line between the eye and the rear sight and the front sight and the target, the shooter maintaining focus on the front sight, and the shooter maintaining even light around the front sight within the rear sight; and displaying the sensory guidance wherein the shooter data analysis tool further comprises a user interface configured to display the sensory guidance.

BRIEF DESCRIPTION OF THE DRAWINGS

FIG. 5 is a top plan view of a shooter observation booth according to an embodiment of the present invention.

FIG. 6 is a lateral view of a shooter observation booth according to an embodiment of the present invention.

DETAILED DESCRIPTION OF THE PREFERRED EMBODIMENT

Figure 1:
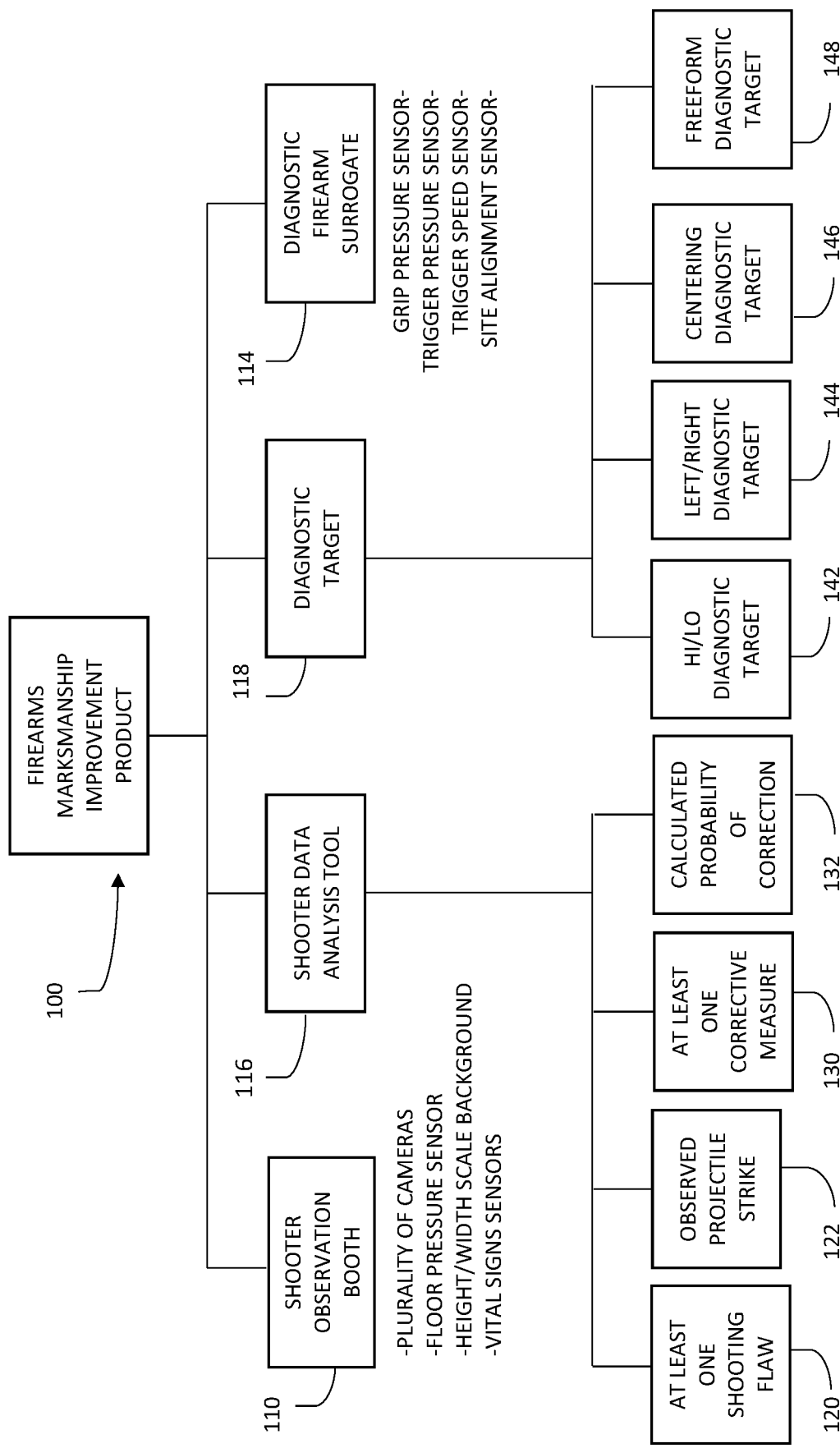
FIG. 1 is a hierarchical chart of characteristics for a firearms marksmanship improvement product according to an embodiment of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

The present disclosure relates to a system and method for the improvement of firearms marksmanship. However, it is understood that the following disclosure provides many different embodiments or examples. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Referring now to FIG. 1, general characteristics of a firearms marksmanship improvement product 100 embodiment are shown. A firearms marksmanship improvement product 100 may include a shooter observation booth, or station, 110 designed to observe flaws in shooting technique. The shooter observation booth 110 may be characterized by intended shooting technique data. For example, and without limitation, a shooter may enter the shooter observation booth 110 equipped with a plurality of cameras 112 for observing and recording shooter data. Shooter data may include, for example, and without limitation, shooter stance, head position, hand position, grip, and trigger pull. The plurality of cameras 112 may be configured to receive a first subset of observed shooting technique data. The first subset of observed shooting technique data may be selected from the group consisting of a stance, a head position, a hand position, a grip, and a trigger pull.

Analysis of the observed shooter data by a shooter data analysis tool 116 may indicate at least one shooting flaw 120 affecting shooting technique, and a corresponding at least one corrective measure 130 suggested to correct the shooting flaw 120. The shooter data analysis tool 116 may also specify at least one corrective measure 130 for correction of a corresponding at least one shooting flaw 120.

Continuing to refer to FIG. 1, the shooter data analysis tool 116 may select the at least one corrective measure 130 based on the at least one shooting flaw 120, an observed projectile strike 122, and a calculated probability of correction 132. The firearms marksmanship improvement product 100 may operate effectively to correct the at least one shooting flaw 120 when the shooter data analysis tool 116 accurately identifies the at least one shooting flaw and accurately selects at least one corrective measure 130 that is likely to correct the at least one shooting flaw.

In more detail, still referring to the invention of FIG. 1, the shooter data analysis tool 116 may select at least one corrective measure 130 when a shooter enters the shooter observation booth 110 armed with a firearm and, in turn, the shooter launches a projectile from the firearm at a target. For example, and without limitation, assuming the plurality of cameras 112 are operational and that a diagnostic target 118 is utilized, the shooter data analysis tool 116 may receive shooter data from the plurality of cameras 112, may observe at least one shooting flaw 120 and may select at least one corrective measure 130 corresponding to the observed shooting flaw. The diagnostic target 118 may be characterized by intended projectile strike data and may be configured to receive observed projectile strike 122 data. Alternatively, the shooter data analysis tool 116 may receive data related to the observed projectile strike 122 and may choose at least one corrective measure 130 corresponding to the observed projectile strike. Further, the shooter data analysis tool 116 may both receive data from the plurality of cameras documenting at least one shooting flaw 120 and may receive data related to the observed projectile strike 122 and may choose at least one corrective measure 130 corresponding to the at least one shooting flaw and the observed projectile strike. The shooter data analysis tool 116 may be configured to determine at least one performance indication, defined as a shooting flaw, using a variance of the intended shooting technique data from the observed shooting technique data and a displacement of the intended projectile strike data from the observed projectile strike 122 data, to determine, using a plurality of known shooting flaws, defined as a plurality of identified shooting flaws, associated with a plurality of known corrective measures, defined as a plurality of identified corrective measures, a probability of correction 132 of the shooting flaw for at least one of the known corrective measures, defined as an applied corrective measure, and provide sensory guidance as to the applied corrective measure. The shooter data analysis tool 116 may further comprise a user interface configured to display the sensory guidance.

Continuing to refer to FIG. 1, assuming that the shooter utilizes a diagnostic firearm surrogate 114 within the shooter observation booth 110, the shooter data analysis tool 116 may consider data relative to shooting technique received from the diagnostic firearm surrogate in order to identify at least one shooting flaw 120 and to select a corresponding at least one corrective measure 130. The diagnostic firearm surrogate 114 may have at least one of a grip pressure sensor 1412 configured to receive the grip and a trigger pressure sensor 1422 configured to receive the trigger pull. For example, and without limitation, the shooter data analysis tool 116 may receive data from the diagnostic firearm surrogate 114, may observe at least one shooting flaw 120 and may select at least one corrective measure 130 corresponding to the observed shooting flaw. The shooter observation booth 110 may further comprise a vital signs sensor configured to receive a third subset of observed shooting technique data selected from the group consisting of a heartrate and a body temperature.

Continuing to refer to FIG. 1, the shooter data analysis tool 116 may consider all data received relative to the shooter, relative to shooting technique, and relative to the target in order to select at least one corrective measure 130. For example, and without limitation, the shooter data analysis tool 116 may select at least one corrective measure 130 based on the at least one shooting flaw 120, whether observed from the plurality of cameras 112 or from the diagnostic firearm surrogate 114, in combination with the observed projectile strike 122.

Factors affecting the selection of at least one corrective measure 130 may include at least one shooting flaw 120 indicated by shooter data or shooting technique data and observed projectile strike 122. For example, and without limitation, at least one shooting flaw 120 indicated by shooter data or shooting technique data may include improper eye to sight alignment, too much grip pressure, anticipation, improper weight distribution, elevated breathing, among others. Alternatively, or in addition, observed projectile strike 122 may reflect shooting low, shooting high, shooting right and/or shooting left. Depending on the observed projectile strike 122, at least one shooting flaw 120 may be indicated as well as a corresponding at least one corrective measure 130. For example, and without limitation, at least one shooting flaw 120 resulting in a projectile strike 122 below the intended bullseye may include anticipating the shot, tilting the head while aiming, improper eye to sight alignment, bad sight picture, and slapping the trigger. For example, and without limitation, at least one shooting flaw 120 resulting in a projectile strike 122 above the intended bullseye may include dropping the head forward while aiming, leaning back while aiming, dropping the wrist while pulling the trigger, improper eye to sight alignment, bad sight picture, and slapping the trigger. For example, and without limitation, at least one shooting flaw 120 resulting in a projectile strike 122 left of the intended bullseye may include incorrect finger placement, over gripping the weapon, milking the grip, tilting the head while aiming, improper eye to sight alignment, bad sight picture, and slapping the trigger. For example, and without limitation, at least one shooting flaw 120 resulting in a projectile strike 122 right of the intended bullseye may include incorrect finger placement, improper eye to sight alignment, bad sight picture, and slapping the trigger.

Continuing to refer to FIG. 1, at least one corrective measure 130 may include, without limitation, breaking the habit of anticipation, correct finger placement on the trigger, correct grip pressure, isolating trigger squeeze in the trigger finger, relaxing shoulders, proper shooting stance, keeping head straight while aiming, proper focus on sites, taking up the slack on the trigger, controlling recoil, keeping the wrist snug, using the correct amount of trigger squeeze, among other corrective measures, all depending upon the at least one shooting flaw 120 observed and/or the observed projectile strike 122. For example, and without limitation, if the observed projectile strike 122 is below the intended bullseye, the at least one corrective measure 130 may include resisting the urge to push against the recoil, keeping the head straight while aiming, centering the front sight within the rear sight, and applying even pressure to the trigger. For example, and without limitation, if the observed projectile strike 122 is above the intended bullseye, the at least one corrective measure 130 may include keeping the head straight while aiming, keeping the centerline of the body straight up and down, keeping the wrist snug while pulling the trigger, centering the front sight within the rear sight, and applying even pressure to the trigger. For example, and without limitation, if the observed projectile strike 122 is to the left of the intended bullseye, the at least one corrective measure 130 may include placing the finger on the trigger so as to be able to draw the trigger straight back toward the web of the hand, gripping the weapon with a correct amount of force gripping the weapon evenly with all of the fingers of the hand, keeping the head straight while aiming, centering the front sight within the rear sight, and applying even pressure to the trigger. For example, and without limitation, if the observed projectile strike 122 is to the right of the intended bullseye, the at least one corrective measure 130 may include placing the finger on the trigger so as to be able to draw the trigger straight back toward the web of the hand, centering the front sight within the rear sight, and applying even pressure to the trigger.

Figure 2:
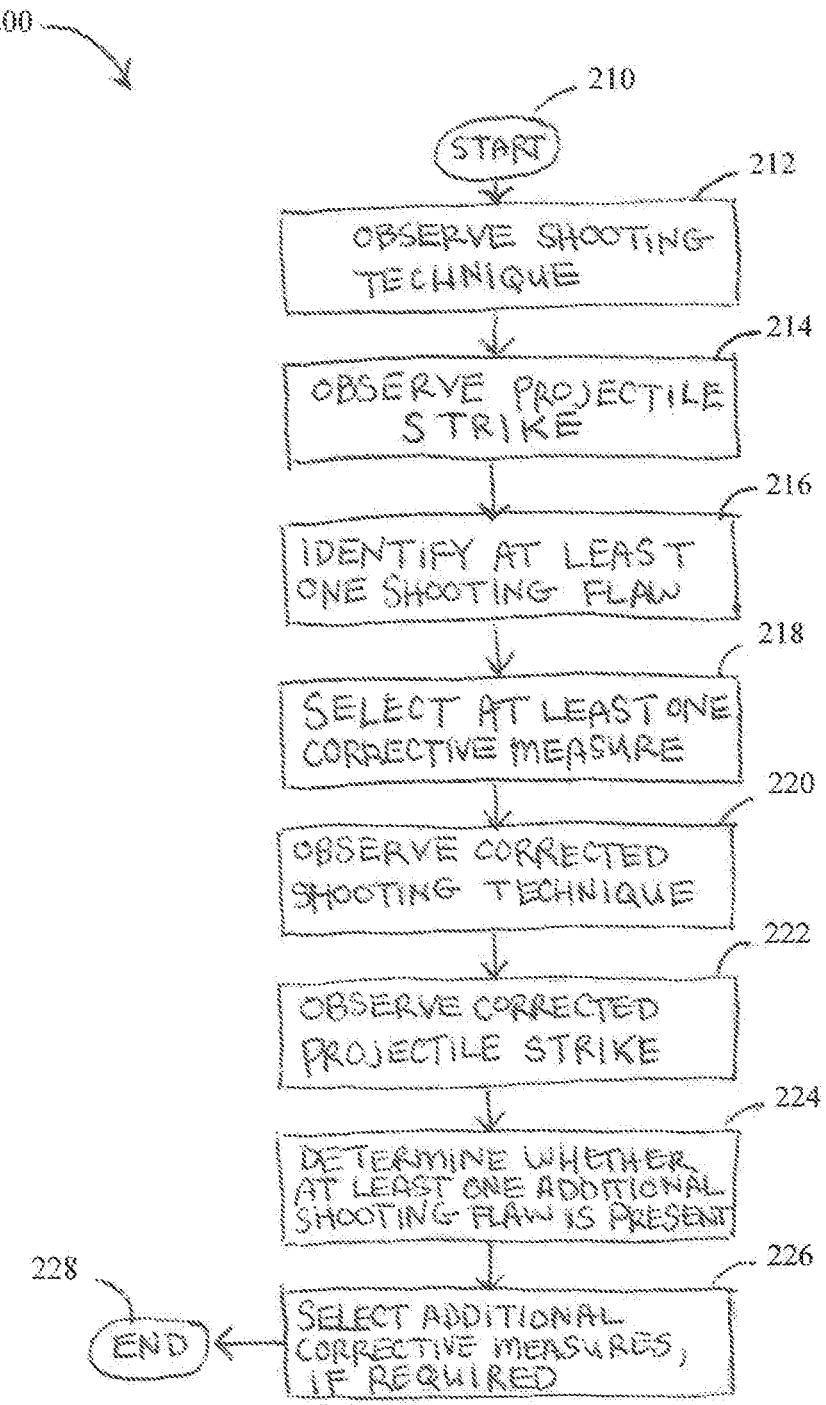
FIG. 2 is a flowchart illustrating a method aspect of an embodiment of the present invention for observing, deducing, and correcting a shooting flaw.

Referring now to FIG. 2, the operation of a method of doing business for identifying, assessing, and correcting at least one shooting flaw by way of a firearms marksmanship improvement product 100 will be discussed. The following illustrative embodiment is included to provide clarity for one operational method that may be included within the scope of the present invention. A person of skill in the art will appreciate additional operations that may be included in identifying, assessing, and correcting at least one shooting flaw by way of a firearms marksmanship improvement product 100 of the present invention, which additional operations are intended to be included herein and without limitation.

From the start, the operation may begin at Block 210, where a shooter may fire a weapon in such a way that shooter data may be observed 212 and the projectile strike may be observed 214. For example, and without limitation, the shooter may fire a weapon in a shooter observation booth 110 equipped with a plurality of cameras 112 and the projectile fired from the weapon may strike a diagnostic target 118. For example, and without limitation, utilizing the observed shooter data and the observed projectile strike 122, a shooter data analysis tool 116 may identify at least one shooting flaw 120 for correction 216. At Block 218, the shooter data analysis tool 116 may select at least one corresponding corrective measure 130 to correct the at least one shooting flaw 120. For example, and without limitation, the shooter data analysis tool 116, may calculate a probability of correction 132 as between a plurality of corrective measures corresponding to the at least one shooting flaw 120 in order to select at least one corrective measure 130 with the highest probability of correcting the at least one shooting flaw. At Block 220 the shooter may again fire a weapon in such a way that shooter data may be observed, and the shooter data analysis tool 116 may determine whether shooting technique has been corrected by utilization of the at least one corrective measure 130. For example, and without limitation, the shooter may again fire a weapon in the shooter observation booth 110 equipped with a plurality of cameras 112, this time implementing the at least one corrective measure 130 selected by the shooter data analysis tool 116, in order to demonstrate a corrected shooting technique. At Block 222 the projectile fired from the weapon may strike the diagnostic target 118, and the shooter data analysis tool 116 may determine whether at least one additional shooting flaw is present 224. In one embodiment, for example and without limitation, the shooter data analysis tool 116, utilizing the observed shooter data and/or the observed projectile strike 122, may determine that at least one additional shooting flaw is present and may select any additional required corrective measures at Block 216. Alternatively, the shooter data analysis tool 116 may determine that no additional shooting flaw is present, at which point the method ends 228.

Generally following the process illustrated by the flowchart 200 in FIG. 2, several variants of methods of doing business are possible. For example, and without limitation, a firearms marksmanship improvement product 100 of the present invention may be in the form of a single shooting flaw 120 (example: slapping the trigger) identified by a shooter data analysis tool 116 and a corresponding single corrective measure 130 (example: even trigger pull) as determined based upon a probability of correction 132 calculated by the shooter data analysis tool 116.

For example, and without limitation, a shooter may launch a projectile from a firearm at a target in a setting suitable for observing data related to the shooter, data related to shooting technique and data related to projectile strike, such as at a gun range equipped with a shooter observation booth 110, at a gun range equipped with diagnostic targets 118, and/or at a gun range equipped with both a shooter observation booth and equipped with diagnostic targets. Alternatively, a shooter may simulate launching a projectile from a firearm at a target in a classroom or other setting equipped with a shooter observation booth 110, a diagnostic firearm surrogate 114 and with an electronic diagnostic target 118. The causes of shooting flaws may vary and, therefore, may require different corrective measures to successfully correct at least one shooting flaw 120, the success of which may depend upon the calculated probability of correction 132 associated with the at least one corrective measure 130 selected. In one embodiment, identification of at least one shooting flaw 120 may result in the selection of at least one corrective measure 130 when a shooter data analysis tool 116 receives data from one or more of a shooter observation booth 110, a diagnostic firearm surrogate 114 and a diagnostic target 118, or a combination of the foregoing, as each may provide data from which to calculate a probability of correction 132 to correct the at least one shooting flaw, observed shooting technique flaw or observed projectile strike flaw.

For example, and without limitation, selecting at least one corrective measure 130 may be as simple as observing a projectile strike 122 on a diagnostic target 118 and selecting a corresponding at least one corrective measure (example: selecting an even trigger pull from the plurality of corrective measures to correct a low and left projectile strike [for a right-handed shooter]) or as complex as calculating the probability of correction 132 in order to select at least one corrective measure from a plurality of corrective measures based on data received from the shooter observation booth 110, the diagnostic firearm surrogate 114 and the diagnostic target (example: data from the shooter observation booth shows that the shooter tilts her head while aiming the firearm; data from the diagnostic firearm surrogate shows that the shooter slaps the trigger when firing the firearm; and data from the diagnostic target shows a low and left projectile strike. The plurality of corrective measures corresponding to the observed data may include, without limitation, maintaining proper head alignment, bringing the firearm sights in line with the eyes, and applying force evenly to the trigger. The shooter data analysis tool 116 may analyze the data received from the shooter observation booth, the diagnostic firearm surrogate, and the diagnostic target and the corresponding corrective measures in order to calculate a probability of correction and, based on that calculation, may select at least one corrective measure to correct the observed shooting flaw). Utilizing data from multiple sources may put upward or downward pressure on the calculated probability of correction 132 depending on the extent to which the data evidences a single shooting flaw or multiple shooting flaws and, in the case of multiple shooting flaws, whether the multiple shooting flaws result in related or unrelated inaccuracies. In one embodiment, upward pressure on calculated probability of correction 132 may occur if only a single shooting flaw is observed or if multiple shooting flaws are observed each of which relate to the same type of shooting inaccuracy. At the same time, observing multiple shooting flaws related to different shooting inaccuracies may put downward pressure on the calculated probability of correction 132. Downward pressure on the calculated probability of correction 132 may also result from the shooter data analysis tool 116 utilizing only a single source of shooter data. Other changed circumstances that may impact the determination of the calculated probability of correction 132 may include, without limitation, the weapon selected, weather conditions, shooter fatigue and wind conditions.

Figure 3:
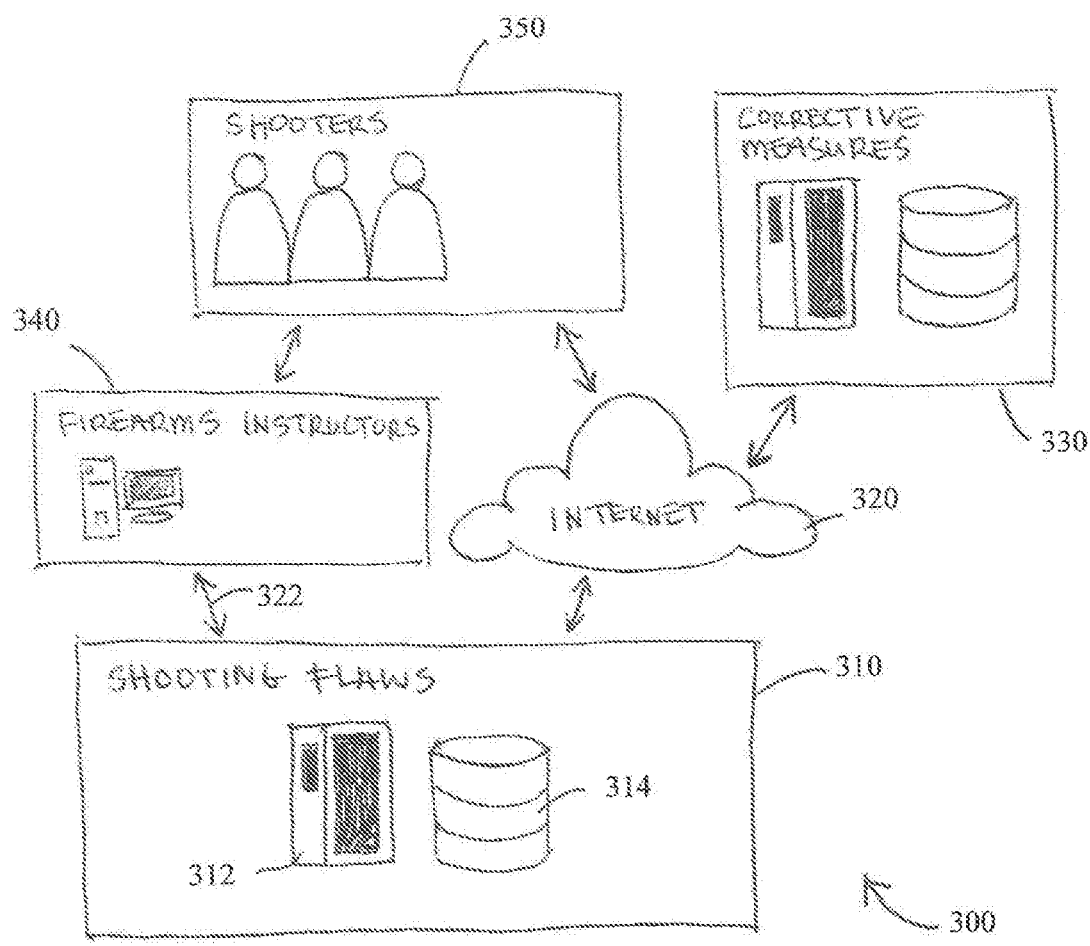
FIG. 3 is a schematic organizational diagram of a computer-based system for processing the method of FIG. 2.

Referring now to FIG. 3, a system 300 for identifying, assessing, and correcting at least one shooting flaw by way of a firearms marksmanship improvement product according to an embodiment of the present invention is now described in greater detail. The system 300 may include a shooter data analysis server 310 that may be configured to be connected with a network 320, such as the Internet. For example, and without limitation, the network 320 may also include a mobile network that may be any type of cellular network device, including GSM, GPRS, CDMA, EV-DO, EDGE, 3G, DECT, OFDMA, WIMAX, and LTE communication devices. These and other communication standards permitting connection to a network 320, such as the Internet, are included within the invention.

The shooter data analysis server 310 may include a central processing unit 312 and a shooting flaw database 314. The shooting flaw database 314 may be configured to support storage and retrieval of shooting flaw information, wherein shooting flaw information is comprised of one or more of the at least one shooting flaw 120 and the observed projectile strike 122. In one embodiment of the present invention, information related to measures for the correction of shooting flaws may be accessed from a corrective measure database 330 and other sources to which a firearms instructor has access, for example, through the Internet. The corrective measure database 330 may be configured to support storage and retrieval of corrective measure information. Accessed information may be recorded in the shooting flaw database 314 and in the corrective measure database 330 for subsequent automated analysis using instructions processed by the central processing unit 312. Using instructions processed by the central processing unit 312, the shooter data analysis server 310 may automatically compare stored shooting flaw information and stored corrective measure information to calculate a probability of correcting the at least one shooting flaw 120. The shooter data analysis server 310 may, based upon the calculated probability of correction 132, automatically select and suggest at least one corrective measure 130.

From a firearms instructor client 340, a user may analyze shooter data and projectile strike information submitted by or on behalf of shooters 350. A user may manage or otherwise manipulate shooting flaw information in the shooting flaw database 314 using a system interface 322 to interact with the shooter data analysis server 310. For example, and without limitation, a local area network (LAN) may support communication between the firearms instructor client 340 and the shooter data analysis server 310.

Figure 4:
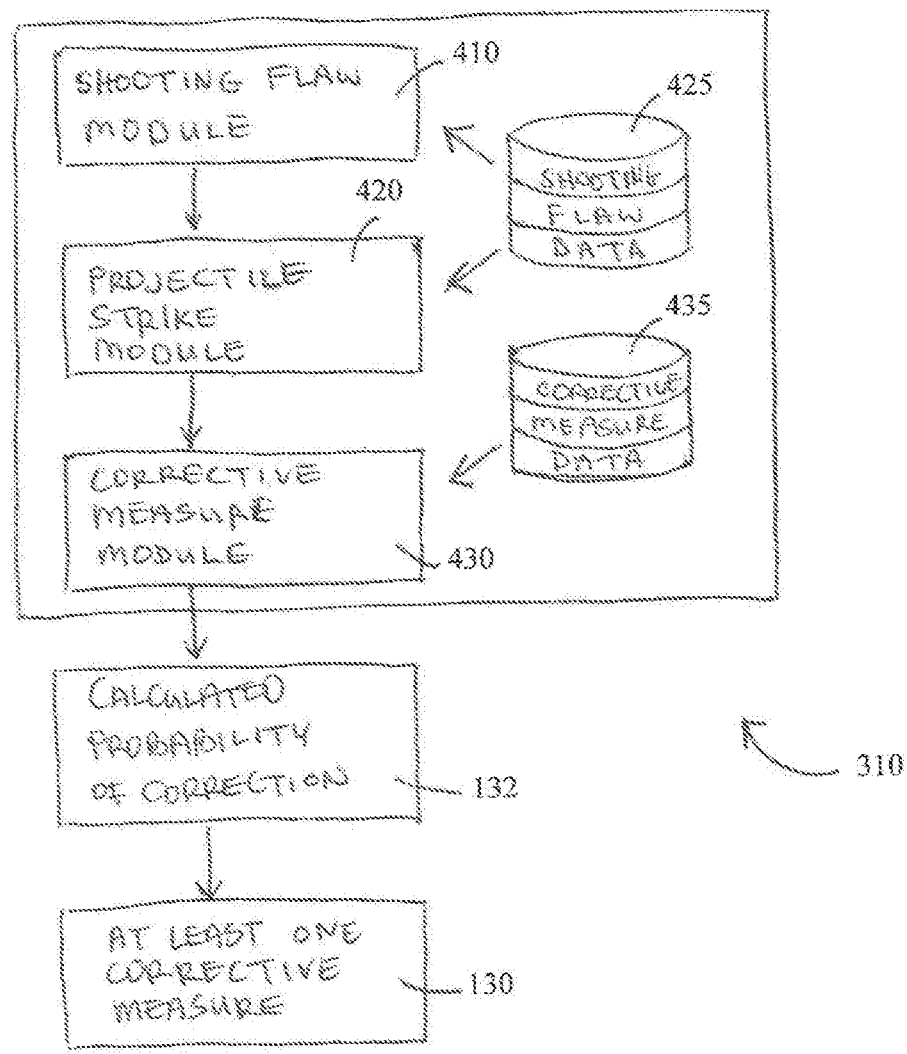
FIG. 4 is a block diagram illustrating a shooter data analysis server component of the computer-based system of FIG. 3.

Referring to FIG. 4, a shooter data analysis server 310 illustrates one embodiment of a system 300 for identifying, assessing, and correcting at least one shooting flaw that may be used to provide a firearms marksmanship improvement product 100. For example, the method 200 of FIG. 2 may be implemented within the shooter data analysis server 310. In the present example, the shooter data analysis server 310 includes a number of components to provide information to a user and to receive and process input from the user. The shooter data analysis server 310 may include executable corrective instructions in the form of a shooting flaw module 410, a projectile strike module 420, and a corrective measure module 430. These modules may utilize information stored in a data store that may contain shooting flaw data 425 and corrective measure data 435. The corrective instructions and the data store may be used to determine a calculated probability of correction 132 as well as at least one corrective measure 130.

Turning now to FIGS. 5-9, a shooter observation booth 110 according to an embodiment of the present invention is described in greater detail. At FIG. 5, a top plan view of the shooter observation booth 110 is illustrated. A top framework 500 may be provided including a first horizontal front piece 510, and an opposite first horizontal back piece 512 connected by a first horizontal side piece 514 and an opposing second horizontal side piece 516. A plurality of cameras 112 may be provided on one or more of the first horizontal front piece 510, the first horizontal back piece 512, the first horizontal side piece 514 and the second horizontal side piece 516. The first horizontal front piece 510, the first horizontal back piece 512, the first horizontal side piece 514 and the second horizontal side piece 516 may be in the form of tubing. Although not illustrated in FIG. 5, the top framework 500 may include intersecting cross pieces. A first horizontal cross piece 520 (depicted in FIG. 9) may connect a midpoint of the first horizontal front piece 510 to a midpoint of the first horizontal back piece 512. A second horizontal cross piece 522 (also depicted in FIG. 9) may connect a midpoint of the first horizontal side piece 514 and a midpoint of the second horizontal side piece 516 with a midpoint of the first horizontal cross piece 520. Alternatively, the first horizontal cross piece 520 may connect an intersection of the first horizontal front piece 510 with the first horizontal side piece 514 to an intersection of the first horizontal back piece 512 with the second horizontal side piece 516. The second horizontal cross piece 522 may connect an intersection of the first horizontal front piece 510 with the second horizontal side piece 516 to the midpoint of the first horizontal cross piece 520 and connect an intersection of the first horizontal back piece 512 with the first horizontal side piece 514 to the midpoint of the first horizontal cross piece 520. The plurality of cameras 112 may be provided on one or more of the first horizontal cross piece 520, the first horizontal side piece 514, the second horizontal cross piece 522 and the second horizontal side piece 516. The plurality of cameras 112 may be disposed so as to observe a shooter and a firearm positioned within the shooter observation booth 110. The plurality of cameras 112 may transmit shooter data to the shooter data analysis tool 116.

Referring now to FIG. 6, a side view of the shooter observation booth 110 is illustrated. A first side framework 600 may be provided including a first vertical front piece 610, and an opposite first vertical back piece 612 connected at a top end thereof by the first horizontal side piece 514 and connected at a bottom end thereof by a third horizontal side piece 616. The third horizontal side piece 616 may be longer than the distance between the first vertical front piece 610 and the first vertical back piece 612, so that the third horizontal side piece extends forward of the first vertical front piece and extends rearward of the first vertical back piece. The plurality of cameras 112 may be provided on one or more of the first vertical front piece 610, the first vertical back piece 612, the first horizontal side piece 514 and the third horizontal side piece 616. The first vertical front piece 610, the first vertical back piece 612, the first horizontal side piece 514 and the third horizontal side piece 616 may be in the form of tubing. Although not illustrated in FIG. 6, the first side framework 600 may include intersecting cross pieces. A third horizontal cross piece 620 may connect a midpoint of the first vertical front piece 610 to a midpoint of the first vertical back piece 612. A first vertical cross piece 622 may connect a midpoint of the first horizontal side piece 514 and a midpoint of the third horizontal side piece 616 with a midpoint of the third horizontal cross piece 620. Alternatively, a first diagonal cross piece 624 (depicted in FIG. 9) may connect an intersection of the first vertical front piece 610 with the first horizontal side piece 514 to an intersection of the first vertical back piece 612 with the third horizontal side piece 616. A second diagonal cross piece 626 may connect an intersection of the first vertical front piece 610 with the third horizontal side piece 616 to a midpoint of the first diagonal cross piece 624 and connect an intersection of the first vertical back piece 612 with the first horizontal side piece 514 to the midpoint of the first diagonal cross piece. The plurality of cameras 112 may be provided on one or more of the first diagonal cross piece 624 and the second diagonal cross piece 626. The plurality of cameras 112 may be disposed so as to observe a shooter and a firearm positioned within the shooter observation booth 110. The plurality of cameras 112 may transmit shooter data to the shooter data analysis tool 116.

A second side framework 600¹ may be provided including a second vertical front piece 610¹, and an opposite second vertical back piece 612¹ connected at a top end thereof by the second horizontal side piece 516 and connected at a bottom end thereof by a fourth horizontal side piece 618. The fourth horizontal side piece 618 may be longer than the distance between the second vertical front piece 610¹ and the second vertical back piece 612¹, so that the fourth horizontal side piece extends forward of the second vertical front piece and extends rearward of the second vertical back piece. The plurality of cameras 112 may be provided on one or more of the second vertical front piece 610¹, the second vertical back piece 612¹, the second horizontal side piece 516 and the fourth horizontal side piece 618. The second vertical front piece 610¹, the second vertical back piece 612¹, the second horizontal side piece 516 and the fourth horizontal side piece 618 may be in the form of tubing. Although not illustrated, the second side framework 600¹ may include intersecting cross pieces. A fourth horizontal cross piece 620¹ may connect a midpoint of the second vertical front piece 610¹ to a midpoint of the second vertical back piece 612¹. A second vertical cross piece 622¹ may connect a midpoint of the second horizontal side piece 516 and a midpoint of the fourth horizontal side piece 618 with a midpoint of the fourth horizontal cross piece 620¹. Alternatively, a third diagonal cross piece 624¹ may connect an intersection of the second vertical front piece 610¹ with the second horizontal side piece 516 to an intersection of the second vertical back piece 612¹ with the fourth horizontal side piece 618. A fourth diagonal cross piece 626¹ may connect an intersection of the second vertical front piece 610¹ with the fourth horizontal side piece 618 to the midpoint of the third diagonal cross piece 624¹ and connect an intersection of the second vertical back piece 612¹ with the second horizontal side piece 516 to the midpoint of the third diagonal cross piece. The plurality of cameras 112 may be provided on one or more of the third diagonal cross piece 624¹ and the fourth diagonal cross piece 626¹. The plurality of cameras 112 may be disposed so as to observe a shooter and a firearm positioned within the shooter observation booth 110. The plurality of cameras 112 may transmit shooter data to the shooter data analysis tool 116.

Figure 7:
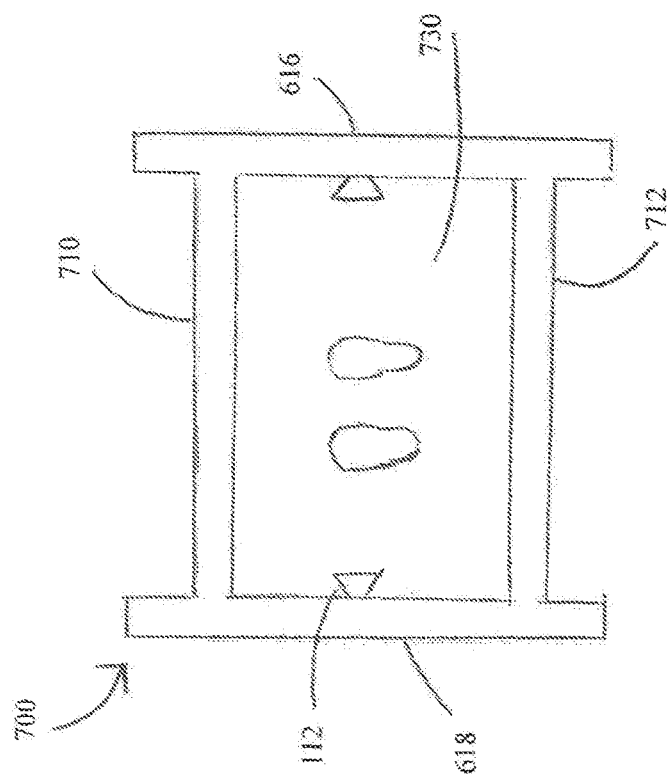
FIG. 7 is a bottom view of a shooter observation booth according to an embodiment of the present invention.

At FIG. 7, a bottom view of the shooter observation booth 110 is illustrated. A bottom framework 700 may be provided including a second horizontal front piece 710, and an opposite second horizontal back piece 712 connected by the third horizontal side piece 616 and the fourth horizontal side piece 618. Although not illustrated, the bottom framework 700 may include intersecting cross pieces. A fifth horizontal cross piece 720 may connect a midpoint of the second horizontal front piece 710 to a midpoint of the second horizontal back piece 712. A sixth horizontal cross piece 722 may connect a midpoint of the third horizontal side piece 616 and a midpoint of the fourth horizontal side piece 618 with a midpoint of the fifth horizontal cross piece 720. Alternatively, the fifth horizontal cross piece 720 may connect an intersection of the second horizontal front piece 710 with the third horizontal side piece 616 to an intersection of the second horizontal back piece 712 with the fourth horizontal side piece 618. Also alternatively, the sixth horizontal cross piece 722 may connect an intersection of the second horizontal front piece 710 with the fourth horizontal side piece 618 to the midpoint of the fifth horizontal cross piece and connect an intersection of the second horizontal back piece 712 with the third horizontal side piece 616 to the midpoint of the fifth horizontal cross piece 720. A pressure sensor 730 may be disposed within the bottom framework. The floor pressure sensor 730 may be configured to receive a second subset of observed shooting technique data selected from the group consisting of a stance and a weight distribution. The second horizontal front piece 710, the second horizontal back piece 712, the fifth horizontal cross piece 720 and the sixth horizontal cross piece 722 may be in a flattened form. The third horizontal side piece 616 and the fourth horizontal side piece 618 may be in the form of tubing. The plurality of cameras 112 may be provided on one or more of the third horizontal side piece 616 and the fourth horizontal side piece 618. The plurality of cameras 112 may be disposed so as to observe a shooter and a firearm positioned within the shooter observation booth 110. The plurality of cameras 112 may transmit shooter data to the shooter data analysis tool 116.

Figure 8:
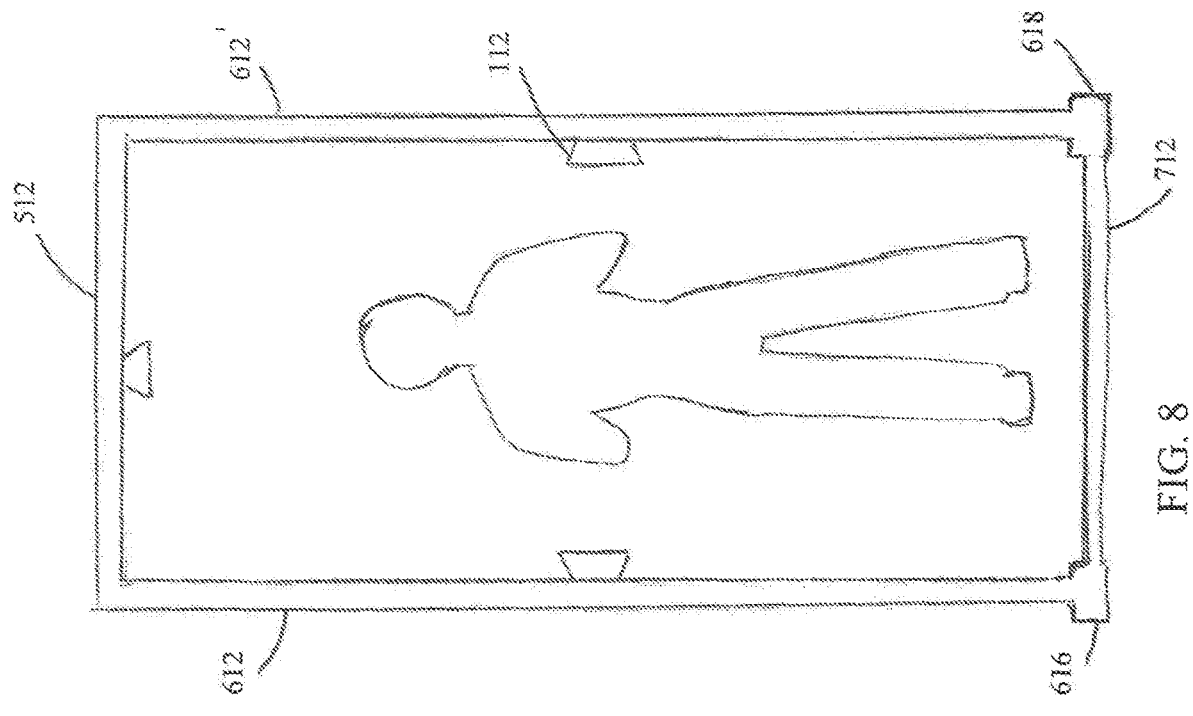
FIG. 8 is a front view of a shooter observation booth according to an embodiment of the present invention.

Referring now to FIG. 8, a rear view of the shooter observation booth 110 is illustrated. A rear framework 800 may be provided including the first vertical back piece 612, and the opposite second vertical back piece 612¹ connected at a top end thereof by the first horizontal back piece 512. The first vertical back piece 612 is connected at a bottom end thereof to the third horizontal side piece 616. The second vertical back piece 612¹ is connected at a bottom end thereof to the fourth horizontal side piece 618. The third horizontal side piece 616 is connected to the fourth horizontal side piece 618 by the second horizontal back piece 712. The plurality of cameras 112 may be provided on one or more of the first vertical back piece 612 and the second vertical back piece 612¹. The first vertical back piece 612, the second vertical back piece 612¹, the first horizontal back piece 512, the third horizontal side piece 616, and the fourth horizontal side piece 618 may be in the form of tubing. The second horizontal back piece 712 may be in a flattened form. Although not illustrated, the rear framework 800 may include intersecting cross pieces. A seventh horizontal cross piece 820 may connect a midpoint of the first vertical back piece 612 to a midpoint of the second vertical back piece 612¹. A third vertical cross piece 822 may connect a midpoint of the first horizontal back piece 512 and a midpoint of the second horizontal back piece 712 with a midpoint of the seventh horizontal cross piece 820. Alternatively, a fifth diagonal cross piece 824 may connect an intersection of the first vertical back piece 612 with the first horizontal back piece 512 to an intersection of the second vertical back piece 612¹ with the second horizontal back piece 712. A sixth diagonal cross piece 826 may connect an intersection of the first vertical back piece 612 with the second horizontal back piece 712 to the midpoint of the fifth diagonal cross piece 824 and connect an intersection of the second vertical back piece 612¹ with the first horizontal back piece to the midpoint of the fifth diagonal cross piece. The plurality of cameras 112 may be provided on one or more of the fifth diagonal cross piece 824 and the sixth diagonal cross piece 826. The plurality of cameras 112 may be disposed so as to observe a shooter and a firearm positioned within the shooter observation booth 110. The plurality of cameras 112 may transmit shooter data to the shooter data analysis tool 116.

A front framework may be provided including the first vertical front piece 610, and the opposite second vertical front piece 610¹ connected at a top end thereof by the first horizontal front piece 510. The first vertical front piece 610 is connected at a bottom end thereof to the third horizontal side piece 616. The second vertical front piece 610¹ is connected at a bottom end thereof to the fourth horizontal side piece 618. The third horizontal side piece 616 is connected to the fourth horizontal side piece 618 by the second horizontal front piece 710. The first vertical front piece 610, the second vertical front piece 610¹, the first horizontal front piece 510, the third horizontal side piece 616, and the fourth horizontal side piece 618 may be in the form of tubing. The second horizontal front piece 710 may be in a flattened form. The plurality of cameras 112 may be provided on one or more of the first vertical front piece 610, the second vertical front piece 610¹ and the first horizontal front piece 510. The plurality of cameras 112 may be disposed so as to observe a shooter and a firearm positioned within the shooter observation booth 110. The plurality of cameras 112 may transmit shooter data to the shooter data analysis tool 116.

Figure 9:
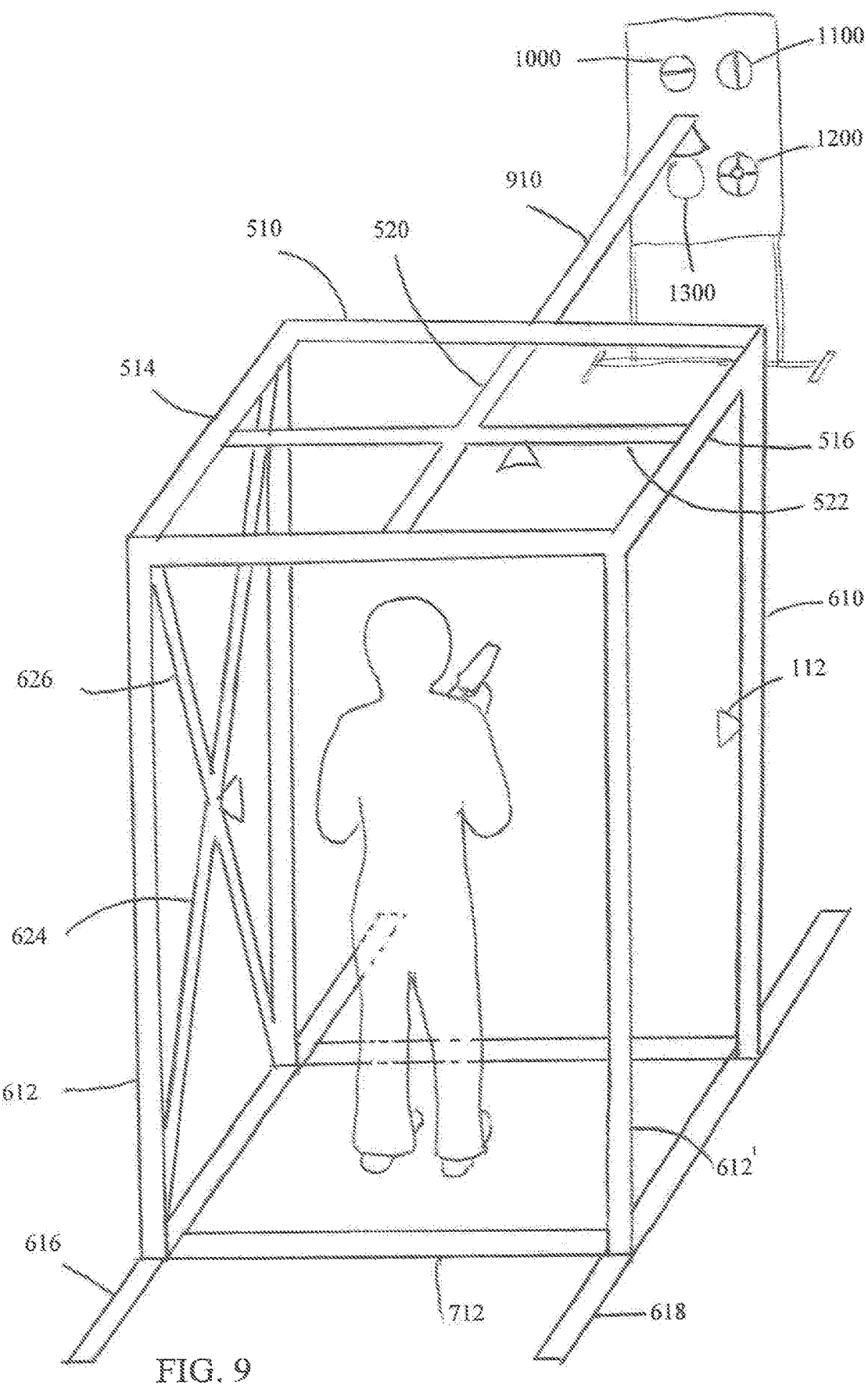
FIG. 9 is a rear view of a shooter observation booth according to an embodiment of the present invention.

Referring now to FIG. 9, a rear perspective view of the shooter observation booth 110 is illustrated. A shooter may be positioned within the shooter observation booth 110. The shooter may be holding a firearm and may be pointing the firearm at a target downrange. An extension arm 910 may be provided extending outwardly from the first horizontal front piece 510. The plurality of cameras 112 may be provided on the extension arm 910. The extension arm 910 may be extendable and retractable so that the positioning of the plurality of cameras may be adjusted. The plurality of cameras 112 may be disposed so as to observe the shooter positioned within the shooter observation booth 110 and the firearm held by the shooter. The plurality of cameras 112 may be disposed so as to observe the target downrange. The plurality of cameras 112 may transmit shooter data to the shooter data analysis tool 116 and may transmit the projectile strike 122 to the shooter data analysis tool.

Although not illustrated, the shooter observation booth 110 may include a removable cover to protect the shooter observation booth and any shooter therein from weather conditions. Although not illustrated, the shooter observation booth 110 may include an image projector. The image projector may project an image of at least one diagnostic target 118, as more particularly described herein, on to a blank target or other suitable surface. Alternatively, the image projector may be provided independent from the shooter observation booth and may be positioned behind a blank target or other suitable surface.

In one embodiment, for example and without limitation, the shooter data observed by the plurality of cameras 112 and/or the projectile strike 122 observed by the plurality of cameras may be transmitted to the shooter data analysis tool 116. The shooter data analysis tool 116 may analyze this shooter data and/or the projectile strike 122 to determine whether at least one shooting flaw 120 is present and may select a corresponding at least one corrective measure 130. Alternatively, the shooter data analysis tool 116 may determine that no shooting flaw is present. The plurality of cameras 112, wherever provided, may be maneuverable so as to change or adjust orientation, direction, or focal point.

Turning now to FIGS. 10-13, at least one diagnostic target 118 according to an embodiment of the present invention is described in greater detail. At FIG. 10, a high/low diagnostic target 1000 according to an embodiment of the present invention is illustrated. The high/low diagnostic target 1000 may include a high/low field 1010 of one color. The high/low field 1010 may have a circular shape. The high/low field may be bisected laterally by a high/low band 1020 of another color. The high/low band 1020 may have a height sufficient to accommodate within the high/low band at least one projectile strike 122. The high/low band 1020 may have a length equal to a diameter of the high/low diagnostic target 1000. Alternatively, the high/low band 1020 may be comprised of a first horizontal line of a color distinct from the high/low field 1010 situated above a second horizontal line of a color distinct from the high/low field. A space may be provided between the first horizontal line and the second horizontal line. The space may have a height sufficient to accommodate within the space at least one projectile strike 122. The space may be colored the same as the high/low field 1010.

Figure 11:
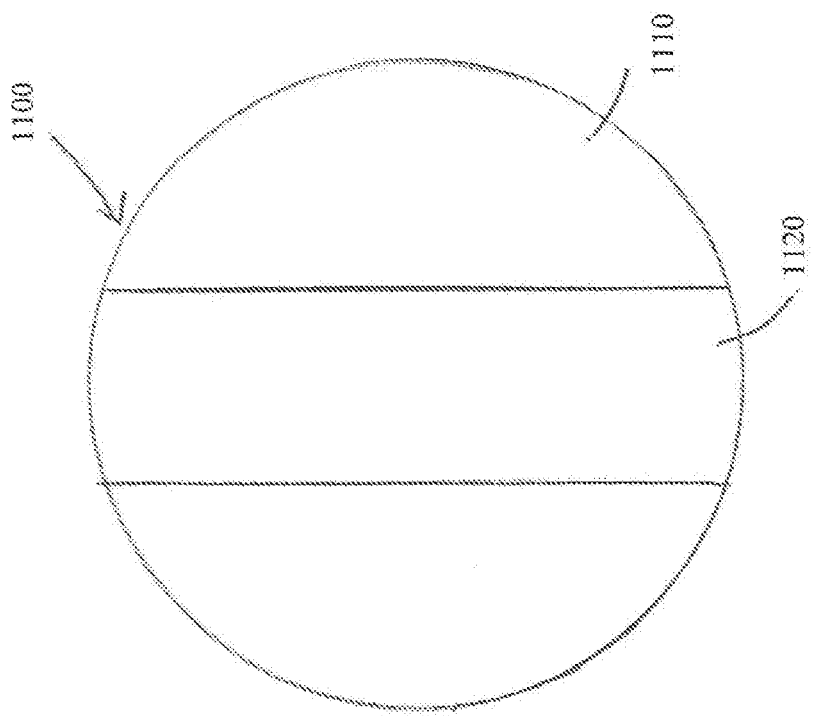
FIG. 11 is a front view of a diagnostic target according to a second exemplary embodiment of the present invention.
Figure 10:
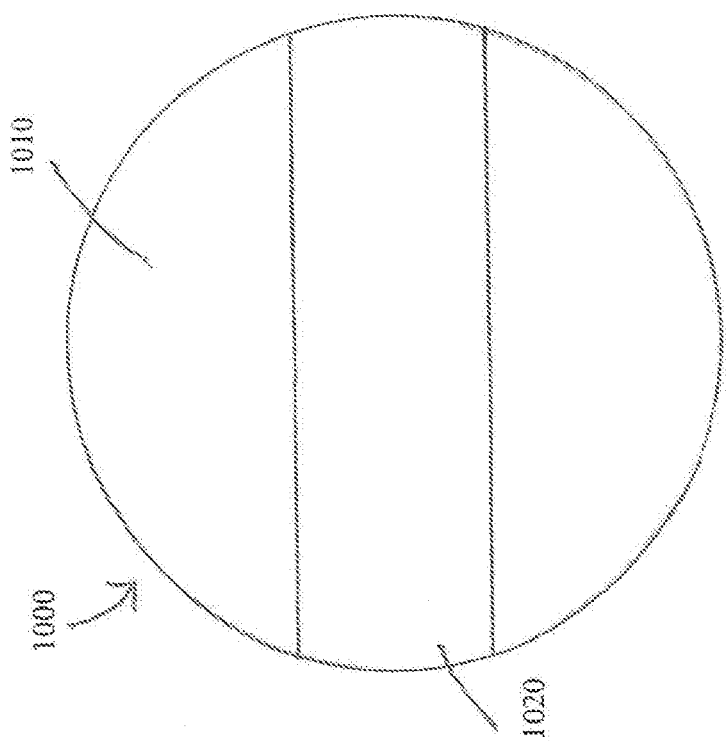
FIG. 10 is a front view of a diagnostic target according to a first exemplary embodiment of the present invention.

At FIG. 11, a left/right diagnostic target 1100 according to an embodiment of the present invention is illustrated. The left/right diagnostic target 1100 may include a left/right field 1110 of one color. The left/right field 1110 may have a circular shape. The left/right field 1110 may be bisected longitudinally by a left/right band 1120 of another color. The left/right band 1120 may have a width sufficient to accommodate within the left/right band at least one projectile strike 122. The left/right band 1120 may have a length equal to a diameter of the left/right diagnostic target 1100. Alternatively, the left/right band 1120 may be comprised of a first vertical line of a color distinct from the left/right field 1110 situated in proximity to a second vertical line of a color distinct from the left/right field. A space may be provided between the first vertical line and the second vertical line. The space may have a width sufficient to accommodate within the space at least one projectile strike 122. Alternatively, the space may have a width sufficient so that, when a shooter is standing 3 yards from the left/right diagnostic target 1100 aiming a firearm at the left/right diagnostic target, the first vertical line aligns with an inner left side of a rear sight of the firearm and the second vertical line aligns with an inner right side of the rear sight of the firearm. The space may be colored the same as the left/right field 1110.

Figure 12:
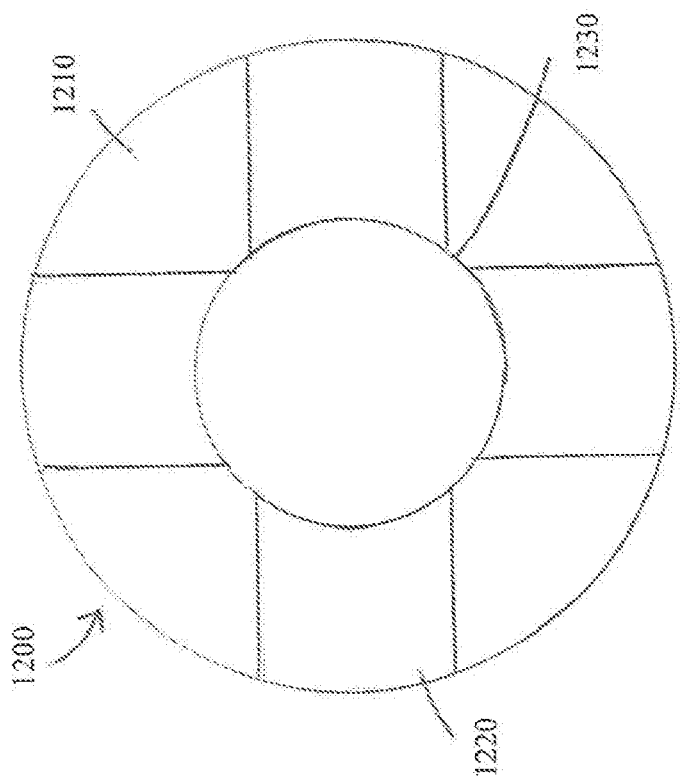
FIG. 12 is a front view of a diagnostic target according to a third exemplary embodiment of the present invention.

At FIG. 12, a grouping diagnostic target 1200 according to an embodiment of the present invention is illustrated. The grouping diagnostic target 1200 may include a grouping field 1210 of one color. The grouping field 1210 may have a circular shape. The grouping diagnostic target 1200 may include an inner field 1230 centered within the grouping field 1210. The inner field 1230 may have a circular shape. The inner field 1230 may have a diameter sufficient to accommodate within the inner field at least one projectile strike 122. The inner field 1230 may be of a color distinct from the color of the grouping field 1210. Alternatively, the inner field 1230 may have a color identical to the color of the grouping field 1210 and may include a border 1232 of a color distinct from the color of the grouping field. A plurality of grouping bands 1220 may emanate from a perimeter of the inner field 1230. The plurality of grouping bands 1220 may extend from the perimeter of the inner field to a perimeter of the grouping field 1210. The plurality of grouping bands 1220 may be oriented such that each of the plurality of grouping bands emanate from cardinal points of the inner field 1230 and extend to cardinal points of the grouping field 1210. Each of the plurality of grouping bands may have a height, in the case of horizontal bands, or a width, in the case of vertical bands, sufficient to accommodate within each of the plurality of grouping bands at least one projectile strike 122.

Figure 13:
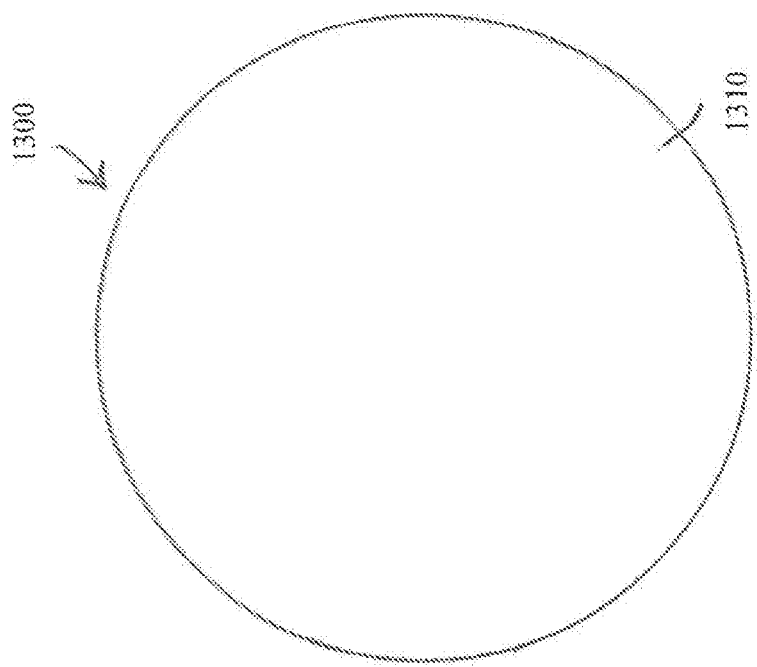
FIG. 13 is a front view of a diagnostic target according to a fourth exemplary embodiment of the present invention.

At FIG. 13, a freelance diagnostic target 1300 according to an embodiment of the present invention is illustrated. The freelance diagnostic target 1300 may include a freelance field 1310 of one color. The freelance field 1310 may have a circular shape. The freelance field 1310 may have a diameter sufficient to accommodate within the freelance field at least one projectile strike 122.

Figure 14:
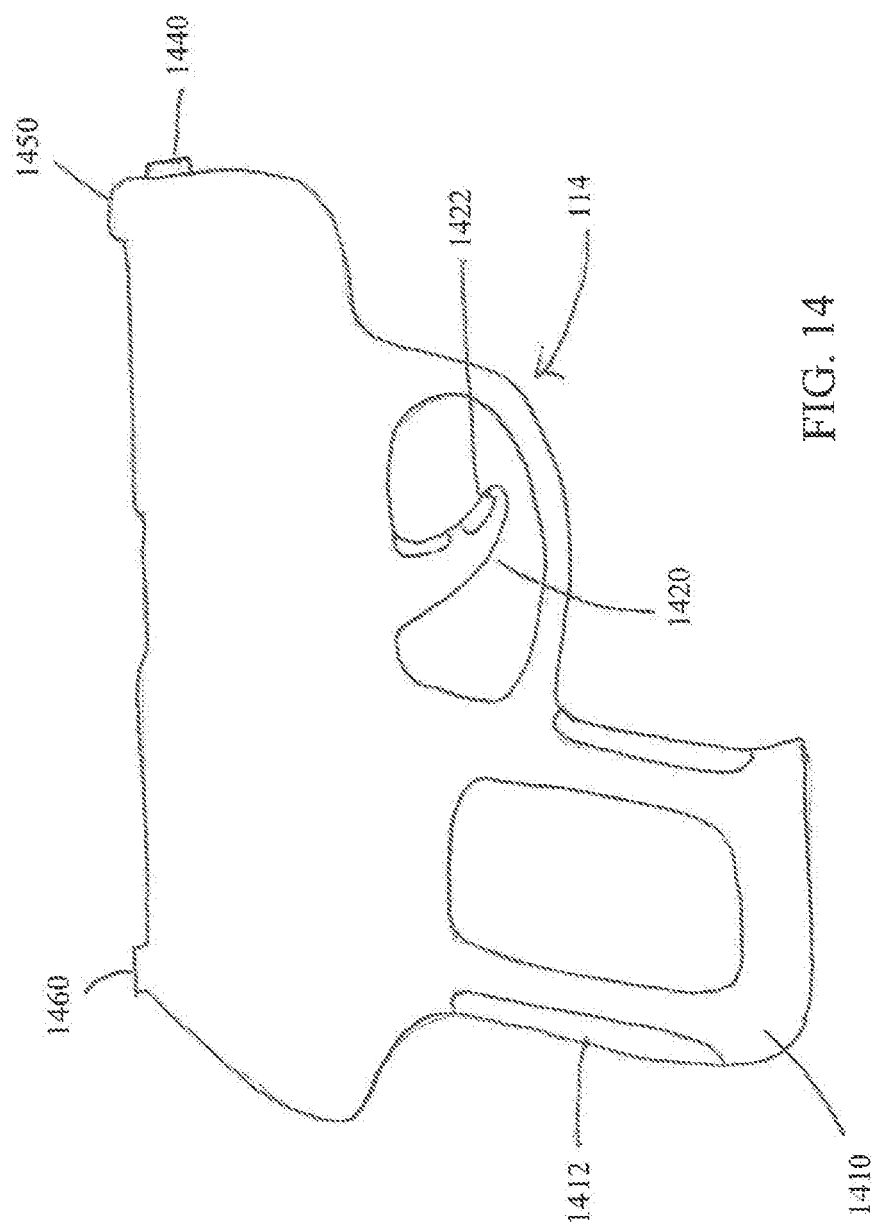
FIG. 14 is a lateral view of a diagnostic firearm surrogate according to an embodiment of the present invention.

Turning now to FIG. 14, a diagnostic firearm surrogate 114 according to an embodiment of the present invention is described in greater detail. The diagnostic firearm surrogate 114 may have a shape, a length, a width, a height, and a weight similar to those of a plurality of actual firearms. The diagnostic firearm surrogate 114 may include a grip 1410. The grip 1410 may include at least one grip pressure sensor 1412. The at least one grip pressure sensor 1412 may transmit a signal to the shooter data analysis tool 116 as shooter data. The diagnostic firearm surrogate 114 may include a trigger 1420. The trigger 1420 may include at least one trigger pressure sensor 1422. The at least one trigger pressure sensor 1422 may transmit a signal to the shooter data analysis tool 116 as shooter data. The diagnostic firearm surrogate 114 may include a discharge simulator 1430. The discharge simulator 1430 may approximate the feeling of a round of ammunition being discharged from the diagnostic firearm surrogate 114. The discharge simulator 1430 may be activated by pulling the trigger 1420. The diagnostic firearm surrogate 114 may include a signal emitter 1440. The signal emitter 1440 may emit a signal in response to pulling the trigger 1420. The signal emitted by the signal emitter 1440 may be in the form of an acoustic signal, an RF signal, an infrared signal, a laser pulse or other wireless media. The diagnostic firearm surrogate 114 may include a front sight 1450 and a rear sight 1460. The front sight 1450, the rear sight 1460, and the signal emitter 1440 may be situated so that when the front sight is properly aligned with the rear sight, the signal emitter may be centered on whatever target at which the diagnostic firearm surrogate 114 may be pointed.

For example, and without limitation, the at least one diagnostic target 118 according to an embodiment of the present invention may be provided by an electronic device, such as a video monitor or a laptop computer screen, equipped with a target sensor capable of receiving an acoustic signal, an RF signal, an infrared signal, a laser pulse or other wireless media and may register the received signal as the projectile strike 122 on the electronic diagnostic target 118. The target sensor may record data related to whether it has been struck and may record data relative to where it has been struck. Alternatively, the at least one diagnostic target 118 may be provided by a virtual reality device which interacts with, and receives signals from, the diagnostic firearm surrogate 114. The virtual reality device may provide a virtual diagnostic target 118 that registers received signals as the projectile strike on the virtual reality diagnostic target 118. The virtual reality device may record data related to whether the virtual reality diagnostic target 118 has been struck and may record data relative to where the virtual reality diagnostic target 118 has been struck. The at least one diagnostic target 118 may be reduced in size in order to approximate longer distances. The target sensor may transmit at least one signal to the shooter data analysis tool 116. The virtual reality device may transmit at least one signal to the shooter data analysis tool 116.

In one embodiment, for example and without limitation, the shooter data signals emitted by the grip pressure sensor 1412 and the shooter data signals emitted by the trigger pressure sensor 1422 and/or the signal recorded by the target sensor as the projectile strike 122 and/or the signal recorded by virtual reality device as the projectile strike 122 may be transmitted to the shooter data analysis tool 116. The shooter data analysis tool 116 may analyze this shooter data and/or the projectile strike 122 to determine whether at least one shooting flaw 120 is present and may select a corresponding at least one corrective measure 130. Alternatively, the shooter data analysis tool 116 may determine that no shooting flaw is present.

It is understood that not every firearms instructor utilizing the systems and methods disclosed herein will be able to correct the shooting flaws exhibited by every shooter. For example, those shooters that do not consistently adopt the at least one corrective measure 130 suggested by the shooter data analysis server may not experience the correction of their at least one shooting flaw 120. In some embodiments, shooters that exhibit more than one shooting flaw, or that do not consistently exhibit the same shooting flaw, may also not experience the correction of their shooting flaw. Those skilled in the art will also recognize that other factors, circumstances, and environmental considerations may contribute to a shooting flaw and may not be corrected utilizing the systems and methods disclosed herein.

Some circumstances may lead a shooter utilizing the systems and methods of the present disclosure to require a live firearms instructor to evaluate particular cases. These cases may fall outside the ambit of the automated systems and methods disclosed herein, but corrective measures may ultimately be provided following review. In such cases, the information obtained by the automated systems and methods disclosed herein may be used for the evaluation. In other embodiments, the information obtained may be supplemented or replaced by additional information obtained by the live firearms instructor. If at least one corrective measure is granted for such exceptional cases, the shooter may be required to continue to deal with the live firearms instructor or may be returned to the automated systems and methods described herein.

Embodiments of the present invention are described herein in the context of a system of computers, servers, and software. Those of ordinary skill in the art will realize that the following embodiments of the present invention are only illustrative and are not intended to be limiting in any way. Other embodiments of the present invention will readily suggest themselves to such skilled persons having the benefit of this disclosure.

Figure 15:
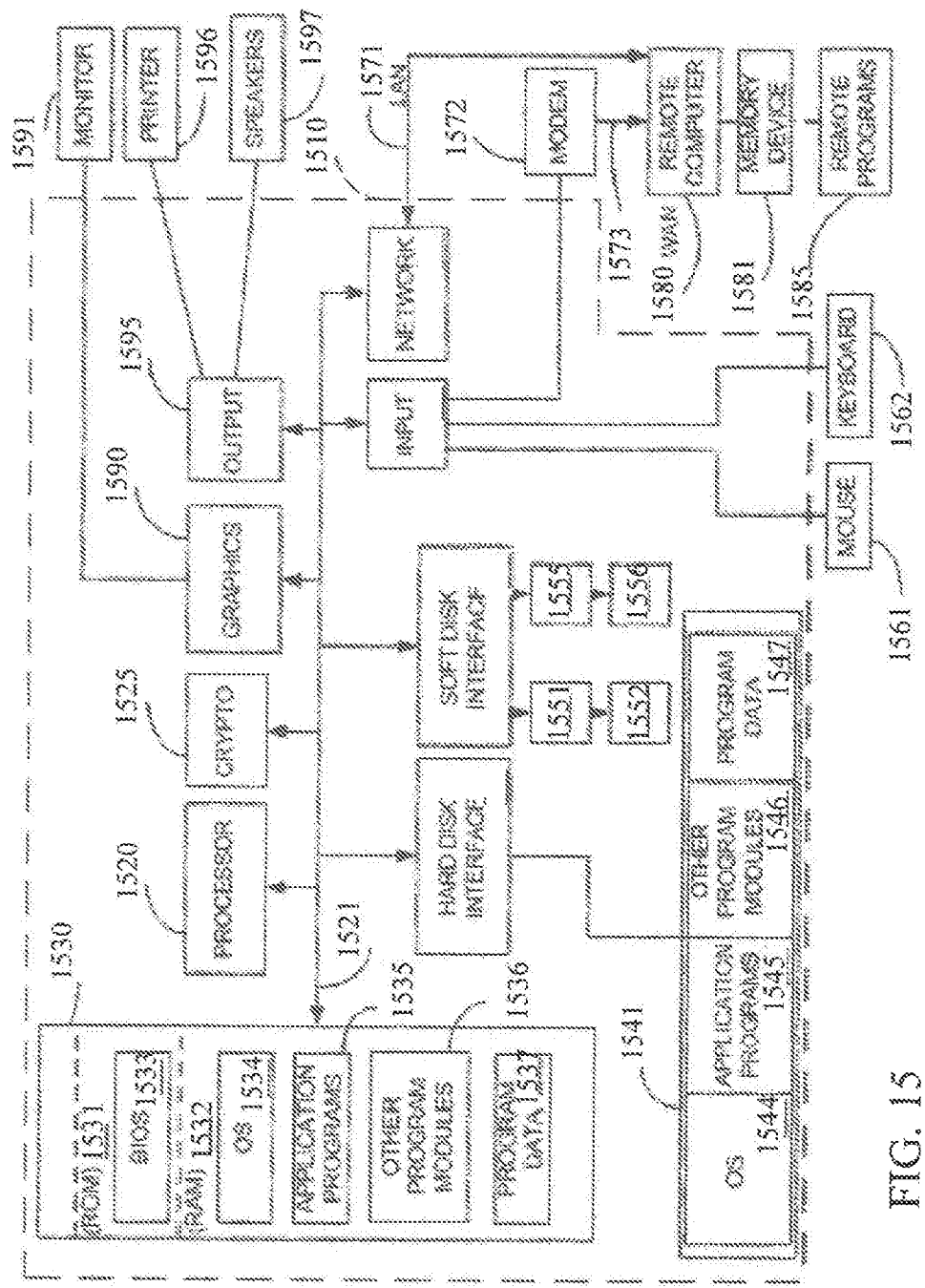
FIG. 15 is a block diagram illustrating a diagrammatic representation of a machine in the example form of a computer system according to an embodiment of the present invention.

A skilled artisan will note that one or more of the aspects of the present invention may be performed on a computing device, including mobile devices. The skilled artisan will also note that a computing device may be understood to be any device having a processor, memory unit, input, and output. This may include, but is not intended to be limited to, cellular phones, smart phones, tablet personal computers (PCs), laptop computers, desktop computers, personal digital assistants (PDAs), etc. FIG. 15 illustrates a model computing device in the form of a computer 1510, which is capable of performing one or more computer-implemented steps in practicing the method aspects of the present invention. Components of the computer 1510 may include, but are not limited to, a processing unit 1520, a system memory 1530, and a system bus 1521 that couples various system components including the system memory to the processing unit 1520. The system bus 1521 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (V ESA) local bus, and Peripheral Component Interconnect (PCI).

The computer 1510 may also include a cryptographic unit 1525. Briefly, the cryptographic unit 1525 has a calculation function that may be used to verify digital signatures, calculate hashes, digitally sign hash values, and encrypt or decrypt data. The cryptographic unit 1525 may also have a protected memory for storing keys and other secret data. In other embodiments, the functions of the cryptographic unit may be instantiated in software and run via the operating system.

A computer 1510 typically includes a variety of computer readable media. Computer readable media can be any available media that can be accessed by a computer 1510 and includes both volatile and nonvolatile media, removable and non-removable media. By way of example, and not limitation, computer readable media may include computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer 610. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer readable media.

The system memory 1530 includes computer storage media in the form of volatile and/or nonvolatile memory such as read only memory (ROM) 1531 and random access memory (RAM) 1532. A basic input/output system 1533 (BIOS), containing the basic routines that help to transfer information between elements within computer 1510, such as during start up, is typically stored in ROM 1531. RAM 1532 typically contains data and/or program modules that are immediately accessible to and/or presently being operated on by processing unit 1520. By way of example, and not limitation, FIG. 15 illustrates an operating system (OS) 1534, application programs 1535, other program modules 1536, and program data 1537.

The computer 1510 may also include other removable/non-removable, volatile/nonvolatile computer storage media. By way of example only, FIG. 15 illustrates a hard disk drive 1541 that reads from or writes to non-removable, nonvolatile magnetic media, a magnetic disk drive 1551 that reads from or writes to a removable, nonvolatile magnetic disk 1552, and an optical disk drive 1555 that reads from or writes to a removable, nonvolatile optical disk 1556 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 1541 is typically connected to the system bus 1521 through a non-removable memory interface such as interface 1540, and magnetic disk drive 1551 and optical disk drive 1555 are typically connected to the system bus 1521 by a removable memory interface, such as interface 1550.

The drives, and their associated computer storage media discussed above and illustrated in FIG. 15, provide storage of computer readable instructions, data structures, program modules and other data for the computer 1510. In FIG. 15, for example, hard disk drive 1541 is illustrated as storing an OS 1544, application programs 1545, other program modules 1546, and program data 1547. Note that these components can either be the same as or different from OS 1534, application programs 1535, other program modules 1536, and program data 1537. The OS 1544, application programs 1545, other program modules 1546, and program data 1547 are given different numbers here to illustrate that, at a minimum, they may be different copies. A user may enter commands and information into the computer 1510 through input devices such as a keyboard 1562 and cursor control device 1561, commonly referred to as a mouse, trackball or touch pad. Other input devices (not shown) may include a microphone, joystick, game pad, satellite dish, scanner, or the like. These and other input devices are often connected to the processing unit 1520 through a user input interface 1560 that is coupled to the system bus, but may be connected by other interface and bus structures, such as a parallel port, game port or a universal serial bus (USB). A monitor 1591 or other type of display device is also connected to the system bus 1521 via an interface, such as a graphics controller 1590. In addition to the monitor, computers may also include other peripheral output devices such as speakers 1597 and printer 1596, which may be connected through an output peripheral interface 1595.

The computer 1510 may operate in a networked environment using logical connections to one or more remote computers, such as a remote computer 1580. The remote computer 1580 may be a personal computer, a server, a router, a network PC, a peer device or other common network node, and typically includes many or all of the elements described above relative to the computer 1510, although only a memory storage device 1581 has been illustrated in FIG. 15. The logical connections depicted in FIG. 15 include a local area network (LAN) 1571 and a wide area network (WAN) 1573, but may also include other networks. Such networking environments are commonplace in offices, enterprise-wide computer networks, intranets and the Internet.

When used in a LAN networking environment, the computer 1510 is connected to the LAN 671 through a network interface or adapter 1570. When used in a WAN networking environment, the computer 1510 typically includes a modem 1572 or other means for establishing communications over the WAN 1573, such as the Internet. The modem 1572, which may be internal or external, may be connected to the system bus 1521 via the user input interface 1560, or other appropriate mechanism. In a networked environment, program modules depicted relative to the computer 1510, or portions thereof, may be stored in the remote memory storage device. By way of example, and not limitation, FIG. 15 illustrates remote application programs 1585 as residing on memory device 1581.

The communications connections 1570 and 1572 allow the device to communicate with other devices. The communications connections 1570 and 1572 are an example of communication media. The communication media typically embodies computer readable instructions, data structures, program modules or other data in a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

In accordance with embodiments of the present invention, the components, process steps, and/or data structures may be implemented using various types of operating systems, computing platforms, computer programs, and/or general purpose machines. In addition, after having the benefit of this disclosure, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

The computer program, according to an embodiment of the present invention, is a computerized system that requires the performance of one or more steps to be performed on or in association with a computerized device, such as, but not limited to, a server, a computer (i.e., desktop computer, laptop computer, netbook, or any machine having a processor), a dumb terminal that provides an interface with a computer or server, a personal digital assistant, mobile communications device, such as a cell phone, smart phone, or other similar device that provides computer or quasi-computer functionality, a mobile reader, such as an electronic document viewer, which provides reader functionality that may be enabled, through either internal components or connecting to an external computer, server, or global communications network (such as the Internet), to take direction from or engage in processes which are then delivered to the mobile reader. It should be readily apparent to those of skill in the art, after reviewing the materials disclosed herein, that other types of devices, individually or in conjunction with an overarching architecture, associated with an internal or external system, may be utilized to provide the "computerized" environment necessary for the at least one process step to be carried out in a machine/system/digital environment. It should be noted that the method aspects of the present invention are preferably computer-implemented methods and, more particularly, at least one step is preferably carried out using a computerized device.

A firearms marksmanship training method comprising the steps of receiving intended shooting technique data and a first subset of observed shooting technique data using a shooter observation booth 110 comprising a plurality of cameras 112; receiving intended projectile strike data and observed projectile strike data 122 using a diagnostic target 118; and determining, using a shooter data analysis tool 116, at least one performance indication, defined as a shooting flaw, as a variance of the intended shooting technique data from the observed shooting technique data and a displacement of the intended projectile strike data from the observed projectile strike data, determining, using the shooter data analysis tool, a probability of correction of the shooting flaw for an applied corrective measure selected from a plurality of known corrective measures, defined as a plurality of identified corrective measures, associated with a plurality of known shooting flaws, defined as a plurality of identified shooting flaws, and providing, using the shooter data analysis tool, sensory guidance as to the applied corrective measure. The shooter data analysis tool 116 may comprise a central processing unit (CPU) 1520 and a non-transitory computer-readable storage medium 1541 accessible through the CPU, and wherein the non-transitory computer-readable storage medium comprises a plurality of instructions executed by the CPU.

While the preceding description shows and describes one or more embodiments, it will be understood by those skilled in the art that various changes in form and detail may be made therein without departing from the spirit and scope of the present disclosure. For example, various steps of the described methods may be executed in a different order or executed sequentially, combined, further divided, replaced with alternate steps, or removed entirely. In addition, various functions illustrated in the methods or described elsewhere in the disclosure may be combined to provide additional and/or alternate functions. As described, some or all of the steps of each method may be implemented in the form of computer executable software instructions. Furthermore, the instructions may be located on a server that is accessible to many different clients, may be located on a single computer that is available to a user, or may be located at different locations. Therefore, the claims should be interpreted in a broad manner, consistent with the present disclosure. While various embodiments have been described for purposes of this disclosure, numerous changes and modifications will be apparent to those of ordinary skill in the art. Such changes and modifications are encompassed within the spirit of this invention as defined by the claims.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

What is claimed is:

1. A firearms marksmanship training system comprising:
a shooter observation station characterized by intended shooting technique data and comprising a plurality of cameras configured to receive a first subset of observed shooting technique data;
a diagnostic target characterized by intended projectile strike data and configured to receive observed projectile strike data; and
a shooter data analysis tool configured to
determine at least one performance indication, defined as a shooting flaw, using a variance of the intended shooting technique data from the observed shooting technique data and a displacement of the intended projectile strike data from the observed projectile strike data,
determine, using a plurality of identified shooting flaws associated with a plurality of identified corrective measures, a probability of correction of the shooting flaw for at least one of the identified corrective measures, defined as an applied corrective measure, and
provide sensory guidance as to the applied corrective measure.

2. The firearms marksmanship training system according to claim 1 wherein the first subset of the observed shooting technique data is selected from the group consisting of a stance, a head position, a hand position, a grip, and a trigger pull.

3. The firearms marksmanship training system according to claim 2 wherein the shooter observation station further comprises a diagnostic firearm surrogate having at least one of a grip pressure sensor configured to receive the grip and a trigger pressure sensor configured to receive the trigger pull.

4. The firearms marksmanship training system according to claim 2 wherein the plurality of cameras is disposed to observe one or more of a shooter positioned within the shooter observation station and a firearm positioned within the shooter observation station and wherein the plurality of cameras is provided on one or more of a position above-and-ahead of the shooter, a position above-and-to-the-left of the shooter, a position above-and-to-the-right of the shooter, a position above-and-behind the shooter, a position above the shooter, a position ahead-and-to-the left of the shooter, a position ahead-and-to-the-right of the shooter, a position behind-and-to-the-left of the shooter, a position behind-and-to-the-right of the shooter, a position to the left of the shooter, a position to the right of the shooter, a position below-and-to-the-left of the shooter, a position below-and-to-the-right of the shooter, and a position behind the shooter, and wherein the plurality of cameras is selectively maneuverable so as to change or adjust an orientation of the plurality of cameras, a direction of the plurality of cameras, or a focal point of a plurality of cameras.

5. The firearms marksmanship training system according to claim 4 wherein the shooter observation station comprises an extension arm affixed to a top portion of the shooter observation station that is selectively extendable and retractable from a front portion of the shooter observation station and wherein the plurality of cameras is disposed on the extension arm to observe one or more of the shooter positioned within the shooter observation station, the firearm positioned within the shooter observation station, and the diagnostic target downrange.

6. The firearms marksmanship training system according to claim 1 wherein the shooter observation station further comprises a floor pressure sensor configured to receive a second subset of the observed shooting technique data selected from the group consisting of a stance and a weight distribution.

7. The firearms marksmanship training system according to claim 1 wherein the shooter observation station further comprises a vital signs sensor configured to receive a third subset of the observed shooting technique data selected from the group consisting of a heartrate and a body temperature.

8. The firearms marksmanship training system according to claim 1 wherein the observed projectile strike data is selected from the group consisting of a low projectile strike, a high projectile strike, a left-of-center projectile strike, a right-of-center projectile strike, a low-and-left-of-center projectile strike, a low-and-right-of-center projectile strike, a high-and-left-of-center projectile strike, and a high-and-right-of-center projectile strike.

9. The firearms marksmanship training system according to claim 1 wherein the plurality of identified shooting flaws is selected from the group consisting of a shooter anticipatorily reacting to a retort of a firearm, the shooter incorrectly locating a trigger-finger on a trigger of the firearm, the shooter gripping the firearm with an incorrect amount of force, the shooter gripping the firearm with an uneven force, the shooter tensing shoulders while shooting the firearm, the shooter incorrectly standing while shooting the firearm, the shooter compromising a straight line between an eye of the shooter and a rear sight of the firearm and a front sight of the firearm and a target, the shooter focusing on a point on the straight line other than the front sight, the shooter failing to maintain control of the trigger, the shooter failing to counteract a recoil of the firearm, the shooter allowing an incorrect amount of slack in a wrist of the shooter, the shooter squeezing the trigger with an incorrect amount of force, and the shooter failing to center the front sight within the rear sight.

10. The firearms marksmanship training system according to claim 9 wherein the plurality of identified corrective actions are selected from the group consisting of the shooter not anticipatorily reacting to the retort of the firearm, the shooter correctly locating the trigger-finger on the trigger of the firearm, the shooter gripping the firearm with a correct amount of force, the shooter gripping the firearm with an even force, the shooter relaxing shoulders while shooting the firearm, the shooter standing with feet apart shoulder-width with knees slightly bent sitting straight down slightly with head straight up, the shooter maintaining control of the trigger release, the shooter pulling the firearm down to counteract recoil, the shooter keeping wrist snug while shooting, the shooter squeezing the trigger straight back to a web of a hand of the shooter with an even force, the shooter maintaining a straight line between the eye and the rear sight and the front sight and the target, the shooter maintaining focus on the front sight, and the shooter maintaining even light around the front sight within the rear sight.

11. The firearms marksmanship training system according to claim 1 wherein the shooter data analysis tool further comprises a user interface configured to display the sensory guidance.

12. A firearms marksmanship training method comprising the steps of:
   receiving intended shooting technique data and a first subset of observed shooting technique data using a shooter observation station comprising a plurality of cameras;
   receiving intended projectile strike data and observed projectile strike data using a diagnostic target; and
   determining, using a shooter data analysis tool, at least one performance indication, defined as a shooting flaw, as a variance of the intended shooting technique data from the observed shooting technique data and a displacement of the intended projectile strike data from the observed projectile strike data,
   determining, using the shooter data analysis tool, a probability of correction of the shooting flaw for an applied corrective measure selected from a plurality of identified corrective measures associated with a plurality of identified shooting flaws, and
   providing, using the shooter data analysis tool, sensory guidance as to the applied corrective measure;
   wherein the shooter data analysis tool comprises a central processing unit (CPU) and a non-transitory computer-readable storage medium accessible through the CPU, and wherein the non-transitory computer-readable storage medium comprises a plurality of instructions executed by the CPU.

13. The firearms marksmanship training method according to claim 12 wherein the first subset of observed shooting technique data is selected from the group consisting of a stance, a head position, a hand position, a grip, and a trigger pull.

14. The firearms marksmanship training method according to claim 13 wherein the shooter observation station comprises a diagnostic firearm surrogate having at least one of a grip pressure sensor and a trigger pressure sensor, and further comprising at least one of the steps of receiving the grip using the grip pressure sensor and receiving the trigger pull using the trigger pressure sensor.

15. The firearms marksmanship training method according to claim 12 wherein the shooter observation booth comprises a floor pressure sensor, and further comprising the step of receiving, using the floor pressure sensor, a second subset of observed shooting technique data selected from the group consisting of a stance and a weight distribution.

16. The firearms marksmanship training method according to claim 12 wherein the shooter observation station comprises a vital signs sensor, and further comprising the step of receiving, using the vital signs sensor, a third subset of observed shooting technique data selected from the group consisting of a heartrate and a body temperature.

17. The firearms marksmanship training method according to claim 12 wherein the observed projectile strike data is selected from the group consisting of a low projectile strike, a high projectile strike, a left-of-center projectile strike, a right-of-center projectile strike, a low-and-left-of-center projectile strike, a low-and-right-of-center projectile strike, a high-and-left-of-center projectile strike, and a high-and-right-of-center projectile strike.

18. The firearms marksmanship training method according to claim 12 wherein the plurality of identified shooting flaws is selected from the group consisting of a shooter anticipatorily reacting to a retort of a firearm, the shooter incorrectly locating a trigger-finger on a trigger of the firearm, the shooter gripping the firearm with an incorrect amount of force, the shooter gripping the firearm with an uneven force, the shooter tensing shoulders while shooting the firearm, the shooter incorrectly standing while shooting the firearm, the shooter compromising a straight line between an eye of the shooter and a rear sight of the firearm and a front sight of the firearm and a target, the shooter focusing on a point on the straight line other than the front sight, the shooter failing to maintain control of the trigger, the shooter failing to counteract a recoil of the firearm, the shooter allowing an incorrect amount of slack in a wrist of the shooter, the shooter squeezing the trigger with an incorrect amount of force, and the shooter failing to center the front sight within the rear sight.

19. The firearms marksmanship training method according to claim 18 wherein the plurality of identified corrective actions is selected from the group consisting of the shooter not anticipating the retort of the firearm, the shooter correctly locating the trigger-finger on the trigger of the firearm, the shooter gripping the firearm with a correct amount of force, the shooter gripping the firearm with an even force, the shooter relaxing shoulders while shooting the firearm, the shooter standing with feet apart shoulder-width with knees slightly bent sitting straight down slightly with head straight up, the shooter maintaining control of the trigger release, the shooter pulling the firearm down to counteract recoil, the shooter keeping wrist snug while shooting, the shooter squeezing the trigger straight back to a web of a hand of the shooter with an even force, the shooter maintaining a straight line between the eye and the rear sight and the front sight and the target, the shooter maintaining focus on the front sight, and the shooter maintaining even light around the front sight within the rear sight.

20. The firearms marksmanship training method according to claim 12 wherein the shooter data analysis tool further comprises a user interface, and further comprising the step of displaying the sensory guidance using the user interface.

* * * * *